United States Patent
Lerner et al.

(10) Patent No.: US 11,633,529 B2
(45) Date of Patent: Apr. 25, 2023

(54) BLOOD FILTRATION SYSTEMS

(71) Applicant: Nuwellis, Inc., Eden Prairie, MN (US)

(72) Inventors: David Lerner, St. Paul, MN (US);
David Haskvitz, Maple Grove, MN (US); Dori Jones, Riverside, CT (US)

(73) Assignee: Nuwellis, Inc., Eden Prairie, MN (US)

( * ) Notice: Subject to any disclaimer, the term of this patent is extended or adjusted under 35 U.S.C. 154(b) by 0 days.

(21) Appl. No.: 17/309,534

(22) PCT Filed: Dec. 31, 2019

(86) PCT No.: PCT/US2019/069130
§ 371 (c)(1),
(2) Date: Jun. 3, 2021

(87) PCT Pub. No.: WO2020/142533
PCT Pub. Date: Jul. 9, 2020

(65) Prior Publication Data
US 2021/0338915 A1    Nov. 4, 2021

Related U.S. Application Data

(60) Provisional application No. 62/787,090, filed on Dec. 31, 2018, provisional application No. 62/787,106, filed on Dec. 31, 2018.

(51) Int. Cl.
*A61M 1/36* (2006.01)
*A61M 1/34* (2006.01)
(Continued)

(52) U.S. Cl.
CPC ........ *A61M 1/3609* (2014.02); *A61M 1/3403* (2014.02); *A61M 1/3431* (2014.02);
(Continued)

(58) Field of Classification Search
CPC ........ A61M 1/0281; A61M 1/14; A61M 1/16; A61M 1/1601; A61M 1/30; A61M 1/34;
(Continued)

(56) References Cited

U.S. PATENT DOCUMENTS 2,693,794 A    11/1954 Vernon
3,256,880 A    6/1966 Caypinar
(Continued)

FOREIGN PATENT DOCUMENTS

CN    107405083 A    11/2017
EP    0596260 A1    5/1994
(Continued)

OTHER PUBLICATIONS

"International Application Serial No. PCT/US2019/068989, International Preliminary Report on Patentability dated Mar. 24, 2021", 8 pgs.
(Continued)

*Primary Examiner* — John Kim
(74) *Attorney, Agent, or Firm* — Schwegman Lundberg & Woessner, P.A.

(57) ABSTRACT

A blood filtration system can reduce the amount of plasma constituents (e.g., water and/or electrolytes) in the blood of the patient, and accordingly increase the hematocrit value of the patient. The blood filtration system (e.g., a controller, or the like) can determine a hematocrit value of a patient. The blood filtration system can determine a venous pressure of vasculature of a patient. The blood filtration system can compensate for pressure head in a component of a blood circuit (e.g., a withdrawal line of a catheter), for example to improve the accuracy of the venous pressure determination. The blood filtration system can determine one or more resistance characteristics of a blood circuit for the blood filtration system. The resistance characteristics can corre-
(Continued)

spond to a resistance to a flow of blood through a component of the blood circuit.

19 Claims, 22 Drawing Sheets

(51) Int. Cl.
- *A61M 60/109* (2021.01)
- *A61M 60/531* (2021.01)
- *A61M 60/546* (2021.01)
- *A61M 60/845* (2021.01)
- *A61M 25/02* (2006.01)

(52) U.S. Cl.
CPC ........ *A61M 1/3496* (2013.01); *A61M 1/3633* (2013.01); *A61M 1/3639* (2013.01); *A61M 25/02* (2013.01); *A61M 60/109* (2021.01); *A61M 60/531* (2021.01); *A61M 60/546* (2021.01); *A61M 60/845* (2021.01); *A61M 2025/0206* (2013.01); *A61M 2025/0253* (2013.01); *A61M 2205/02* (2013.01); *A61M 2205/3334* (2013.01); *A61M 2205/3344* (2013.01); *A61M 2205/3365* (2013.01); *A61M 2210/083* (2013.01); *A61M 2230/207* (2013.01); *A61M 2230/30* (2013.01)

(58) Field of Classification Search
CPC .. A61M 1/3403; A61M 1/3406; A61M 1/341; A61M 1/3413; A61M 1/3417; A61M 1/3427; A61M 1/3434; A61M 1/3482; A61M 1/3496; A61M 1/36; A61M 1/3609; A61M 1/3621; A61M 1/3633; A61M 1/3639; A61M 1/3653; A61M 1/3656; A61M 1/38; A61M 1/382; A61M 1/385; A61M 2230/207
See application file for complete search history.

(56) References Cited

U.S. PATENT DOCUMENTS

| | | |
|---|---|---|
| 3,625,210 A | 12/1971 | Mikkelson |
| 3,722,508 A | 3/1973 | Roberts |
| 3,812,851 A | 5/1974 | Rodriguez |
| 4,340,041 A | 7/1982 | Frank |
| 4,370,977 A | 2/1983 | Mauldin et al. |
| 4,470,410 A | 9/1984 | Elliott |
| 4,502,477 A | 3/1985 | Lewis |
| 4,538,595 A | 9/1985 | Hajianpour |
| 4,624,247 A | 11/1986 | Ford |
| 4,657,000 A | 4/1987 | Hepburn |
| 4,664,129 A | 5/1987 | Helzel et al. |
| 4,697,583 A | 10/1987 | Mason et al. |
| 4,771,768 A | 9/1988 | Crispin |
| 4,817,588 A | 4/1989 | Bledsoe |
| 5,052,379 A | 10/1991 | Airy et al. |
| 5,263,497 A | 11/1993 | Grabenkort et al. |
| 5,337,737 A | 8/1994 | Rubin et al. |
| 5,413,120 A | 5/1995 | Grant |
| 5,749,840 A | 5/1998 | Mitchell et al. |
| 5,897,519 A | 4/1999 | Shesol et al. |
| 6,042,568 A | 3/2000 | Gomez |
| 6,113,577 A | 9/2000 | Hakky et al. |
| 6,117,097 A | 9/2000 | Ruiz |
| 6,238,360 B1 | 5/2001 | Gildersleeve et al. |
| 6,464,669 B2 | 10/2002 | Wilke |
| 6,585,675 B1 | 7/2003 | O'Mahony et al. |
| 6,695,806 B2 | 2/2004 | Gelfand et al. |
| 6,796,955 B2 | 9/2004 | O'Mahony et al. |
| 6,879,850 B2 | 4/2005 | Kimball |
| 6,979,306 B2 | 12/2005 | Moll |
| 7,074,202 B1 | 7/2006 | Weber et al. |
| 7,479,122 B2 | 1/2009 | Ceriani et al. |
| 7,988,653 B2 | 8/2011 | Fout et al. |
| 8,292,838 B2 | 10/2012 | Ingimundarson et al. |
| 8,376,978 B2 | 2/2013 | Roger et al. |
| 9,295,773 B2 | 3/2016 | Prosl et al. |
| 9,345,606 B2 | 5/2016 | Bonutti et al. |
| 9,358,147 B1 | 6/2016 | Ancinec |
| 9,480,455 B2 | 11/2016 | Buckberry |
| 9,572,702 B2 | 2/2017 | Bonutti et al. |
| 9,918,864 B2 | 3/2018 | Grant et al. |
| 9,943,316 B2 | 4/2018 | Kornowski et al. |
| 9,950,105 B2 | 4/2018 | Roger et al. |
| 10,561,881 B2 | 2/2020 | Matsuura et al. |
| 11,382,784 B2 | 7/2022 | Vogel et al. |
| 2001/0007930 A1 | 7/2001 | Kleinekofort |
| 2002/0026135 A1 | 2/2002 | Lowe |
| 2003/0125651 A1 | 7/2003 | Hopkins et al. |
| 2003/0152482 A1 | 8/2003 | Omahony et al. |
| 2004/0011740 A1 | 1/2004 | Bernard et al. |
| 2004/0030277 A1 | 2/2004 | Omahony et al. |
| 2005/0197585 A1 | 9/2005 | Brockway et al. |
| 2006/0161211 A1 | 7/2006 | Thompson et al. |
| 2007/0112289 A1 | 5/2007 | Cavalcanti et al. |
| 2007/0155588 A1 | 7/2007 | Stark et al. |
| 2007/0270672 A1 | 11/2007 | Hayter |
| 2008/0071224 A1 | 3/2008 | Forsyth et al. |
| 2009/0024065 A1 | 1/2009 | Einarsson |
| 2010/0187176 A1 | 7/2010 | Del Canizo Lopez |
| 2010/0331754 A1 | 12/2010 | Fulkerson et al. |
| 2011/0108482 A1 | 5/2011 | Lovell |
| 2011/0155148 A1 | 6/2011 | Golden et al. |
| 2011/0224499 A1 | 9/2011 | Banet et al. |
| 2013/0184627 A1 | 7/2013 | Vedder et al. |
| 2013/0248450 A1 | 9/2013 | Kenley et al. |
| 2013/0261529 A1 | 10/2013 | O'mahony |
| 2014/0060547 A1 | 3/2014 | Vallino et al. |
| 2014/0217027 A1 | 8/2014 | Meyer et al. |
| 2015/0190096 A1 | 7/2015 | Zong et al. |
| 2016/0158082 A1 | 6/2016 | Gainor et al. |
| 2016/0287426 A1 | 10/2016 | Kimmer et al. |
| 2017/0021137 A1 | 1/2017 | Cole |
| 2017/0065448 A1 | 3/2017 | Michell |
| 2017/0258993 A1 | 9/2017 | Pizzochero et al. |
| 2018/0000394 A1 | 1/2018 | Black et al. |
| 2018/0217168 A1 | 8/2018 | Feldschuh et al. |
| 2018/0243517 A1 | 8/2018 | Edwards |
| 2021/0346651 A1 | 11/2021 | Lerner et al. |
| 2021/0379264 A1 | 12/2021 | Lerner et al. |

FOREIGN PATENT DOCUMENTS

| | | |
|---|---|---|
| EP | 1480713 | 11/2013 |
| EP | 3190421 A1 | 12/2017 |
| WO | 2010124389 | 11/2010 |
| WO | WO-2020142454 A1 | 7/2020 |
| WO | WO-2020142533 A1 | 7/2020 |

OTHER PUBLICATIONS

"International Application Serial No. PCT/US2019/068989, International Search Report dated May 4, 2020", 5 pgs.
"International Application Serial No. PCT/US2019/068989, Invitation to Pay Additional Fees dated Mar. 12, 2020", 3 pgs.
"International Application Serial No. PCT/US2019/068989, Written Opinion dated May 4, 2020", 7 pgs.
"International Application Serial No. PCT/US2019/069130, International Preliminary Report on Patentability dated May 6, 2021", 25 pgs.
"International Application Serial No. PCT/US2019/069130, International Search Report dated May 26, 2020", 6 pgs.
"International Application Serial No. PCT/US2019/069130, Invitation to Pay Additional Fees dated Apr. 3, 2020", 3 pgs.
"International Application Serial No. PCT/US2019/069130, Written Opinion dated May 26, 2020", 22 pgs.
"U.S. Appl. No. 17/309,298, Non Final Office Action dated Sep. 3, 2021", 20 pages.

(56) References Cited

OTHER PUBLICATIONS

"European Application Serial No. 19907123.4, Extended European Search Report dated Nov. 15, 2021", 9 pages.
"U.S. Appl. No. 17/309,298, Response filed Dec. 2, 2021 to Non Final Office Action dated Sep. 3, 2021", 15 pgs.
"U.S. Appl. No. 17/309,298, Examiner Interview Summary dated Dec. 6, 2021", 3 pgs.
"European Application Serial No. 19907349.5, Extended European Search Report dated Dec. 14, 2021", 9 pgs.
"U.S. Appl. No. 17/309,298, Final Office Action dated Jan. 7, 2022", 18 pgs.
"U.S. Appl. No. 17/309,298, Response filed Mar. 7, 2022 to Final Office Action dated Jan. 7, 2022", 14 pgs.
"U.S. Appl. No. 17/309,298, Advisory Action dated Mar. 21, 2022", 3 pgs.
"U.S. Appl. No. 17/309,298, Response filed Apr. 6, 2022 to Advisory Action dated Mar. 21, 2022", 13 pgs.
"U.S. Appl. No. 17/309,298, Final Office Action dated Sep. 1, 2022", 34 pgs.
"U.S. Appl. No. 17/309,298, Non Final Office Action dated Apr. 26, 2022", 20 pgs.
"U.S. Appl. No. 17/309,298, Response filed Jul. 26, 2022 to Non Final Office Action dated Apr. 26, 2022", 25 pgs.
"European Application Serial No. 19907123.4, Response filed Jun. 13, 2022 to Extended European Search Report dated Nov. 15, 2021", 48 pgs.
"European Application Serial No. 19907349.5, Response filed Jul. 20, 2022 to Extended European Search Report dated Dec. 14, 2021", 41 pgs.

BLOOD FILTRATION SYSTEMS

CLAIM OF PRIORITY

This patent application claims the benefit of priority of Lerner et al., U.S. Provisional Patent Application Ser. No. 62/787,106, titled "BLOOD FILTRATION SYSTEMS," filed on Dec. 31, 2018; and Lerner et al., U.S. Provisional Patent Application Ser. No. 62/787,090, titled "BLOOD FLOW ASSISTING PORTABLE ARM SUPPORT," filed on Dec. 31, 2018 the benefit of priority of each of which is claimed hereby, and each of which are incorporated by reference herein in its entirety.

CROSS-REFERENCE TO RELATED PATENT DOCUMENTS

This patent U.S. patent application Ser. No. 17/309,298, is also related to the application titled "BLOOD FLOW ASSISTING PORTABLE ARM SUPPORT" by Lerner et al., filed on May 17, 2021, which is hereby incorporated by reference herein in its entirety.

TECHNICAL FIELD

This document pertains generally, but not by way of limitation, to medical devices.

BACKGROUND

A blood filtration system can remove blood from the blood stream (e.g., venous circulation) of a patient and separate plasma water and electrolytes from erythrocytes (e.g., red blood cells) and other blood constituents by means of a filter. The system can convey the plasma water to a reservoir (e.g., a bag) for disposal. The balance of the plasma water, the erythrocytes, and other blood constituents are returned to the patient's blood stream. Once blood is withdrawn from the blood stream and makes contact with extracorporeal components of the blood filtration system (e.g., tubing, the filter, or the like), a potential exists for clots to form within the extracorporeal components, leading to an increase in resistance within the components (e.g., the filter), and potentially clogging (e.g., occluding) the components. While not harmful to the patient, the increase in resistance or clotting could necessitate replacement of one or more of the extracorporeal components.

SUMMARY

The hematocrit value in a patient is a ratio of the red blood cell volume to the total volume of blood in a patient, where the total volume of blood includes the red blood cell volume and the volume of plasma (including, but not limited to water, proteins, and electrolytes) in the blood of the patient. In some examples, a patient experiencing congestive heart failure can have excess plasma volume, and accordingly a reduced hematocrit value. For instance, the patient can have excess plasma water that correspondingly increases the plasma volume of the patient (and lowers the hematocrit value of the patient). A blood filtration system can reduce the amount of plasma constituents (e.g., water and/or electrolytes) in the blood of the patient, and accordingly increase the hematocrit value of the patient.

The present inventors have recognized, among other things, that a problem to be solved can include improving the accuracy of a hematocrit value determination (e.g., measurement, assessment, evaluation, computation, or the like). Additionally, the present inventors have recognized, among other things, that a problem to be solved can include determining if a hematocrit value determination is affected by movement of a patient (e.g., when a patient transitions from a supine position to a standing position). Further, the present inventors have recognized, among other things, that a problem to be solved can include determining the amount of plasma remaining in the patient.

Still further, the present inventors have recognized, among other things, that a problem to be solved can include determining a rate of removing plasma constituents while maintaining preferred patient diagnostic parameters (e.g., vital signs, for instance vascular resistance, venous pressure or the like). Still yet further, the present inventors have recognized, among other things, that a problem to be solved can include determining when to cease removal of the plasma constituents from the blood stream to obtain a preferred hematocrit value (e.g., euvolemia, or a preferred amount of blood in the patient) in the patient. Additionally, the present inventors have recognized, among other things, that a problem to be solved can include reducing clogging of the extracorporeal components of a blood filtration system.

The present subject matter can help provide a solution to this problem, such as by providing a blood filtration system. The blood filtration system can reduce one or more plasma constituents in blood of a patient. The blood filtration system can include a variable-speed blood pump that can be configured to pump blood in a withdrawal line, through a filter, and into an infusion line. The withdrawal line and the infusion line can be configured to couple with a catheter, and the catheter can be configured for insertion into a blood stream of the patient. The withdrawal line and the infusion line can be configured to couple with the filter. The filter can be configured to reduce an amount of one or more plasma constituents in blood flowing through the filter and provide a filtrate fluid including the plasma constituents. The blood filtration system can include a variable speed filtration pump that can be configured to extract the filtrate fluid from the filter.

The blood filtration system can include a controller including processing circuitry. The controller can be configured to control the speed of the blood pump to vary the flow rate of the blood through the filter. Additionally, the controller can be configured to control the speed of the filtration pump to vary the extraction rate of the filtrate fluid from the filter. Further, the controller can be configured to determine the venous pressure of the patient. Still further, the controller can be configured to provide a notification of the venous pressure of the patient (e.g., providing a notification on a display). In some examples, the blood filtration system can determine the venous pressure of the patient by controlling the speed of the blood pump to stop the blood pump. The blood filtration system can determine the venous pressure of the patient because the blood filtration system can be in communication with the blood stream of the patient.

Additionally, the controller can be configured to determine a hematocrit value of the patient. In an example, determining the hematocrit value of the patient includes controlling the speed of the blood pump and setting the flow rate of blood through the filter. Controlling the speed of the blood pump can improve the accuracy of the hematocrit value determination. For instance, the hematocrit value determination by an optical hematocrit sensor can be affected by the flow rate of blood through the filter. In this example, the speed of the blood pump can vary, and the determined hematocrit value of the patient can vary according to the speed of the blood pump. Accordingly, measuring the hematocrit value with the blood pump at a consistent speed can improve the accuracy of the hematocrit value determination.

Further, the controller can be configured to determine if movement of the patient from an initial position affects the determined hematocrit value of the patient. For instance, a sensor can be configured to monitor movement of the patient relative to the initial position of the patient. The controller can be configured to provide a notification if the hematocrit determination is affected by the movement of the patient. In an example, the controller can provide a notification (e.g., on a display) with a timer since the patient moved in a way that affected the hematocrit value determination. In another example, the controller can refrain from providing a notification of the hematocrit value when the hematocrit value is affected by movement of the patient (e.g., by refraining from displaying the movement-affected hematocrit value on a display). Accordingly, the blood filtration system can provide additional information (e.g., to a healthcare provider) that the hematocrit value of the patient has been affected by movement of the patient.

Further, the controller can be configured to change a filtration rate that the one or more plasma constituents are extracted from the filter. For instance, the controller can control a speed of a filtration pump to change the extraction rate of the plasma constituents from the filter. The filtration rate can be changed (e.g., increased or decreased) a specified of amount, and the controller can determine the hematocrit value of the patient (or a rate of change of the hematocrit value of the) before and after the change in filtration rate. In some examples, the amount of change of the filtration rate and the determined hematocrit values before and after the change in filtration rate can be used to determine the amount of plasma constituents remaining in a patient. Determining the amount of plasma constituents remaining in the patient can be used to determine how much of the plasma constituents the blood filtration system should extract from the patient.

Still further, the controller can be configured to control a speed of one or more pumps to adjust a filtration fraction of the system. The filtration fraction can include a ratio of a filtration rate (e.g., a rate that one or more plasma constituents is extracted from the filter) to a blood flow rate through the filter. The controller can vary the speed of the one or more pumps (e.g., the filtration pump, the blood pump, or the like) to adjust the filtration fraction. Additionally, the controller can be configured to determine the hematocrit value, and can compare the hematocrit value to a hematocrit threshold. The controller can be configured to maintain the filtration fraction, for instance when the hematocrit value equals the hematocrit threshold. Further, the controller can be configured to adjust the filtration fraction, for instance if the hematocrit value exceeds, or declines below, the hematocrit threshold. In some examples, the hematocrit threshold is a range of hematocrit values (e.g., 45 percent to 55 percent). Controlling the filtration fraction can be used to control the rate of removing plasma constituents while maintaining preferred patient diagnostic parameters. Additionally, controlling the filtration fraction can be used to reduce clogging of the extracorporeal components of a blood filtration system. For instance, when the hematocrit value is high (e.g., greater than 50 percent) the filter can have an increased probability of clogging). In some examples, the filtration fraction can be reduced (e.g., filtration rate reduced, blood flow rate increased, or a combination thereof) to reduce the probability of clogging in the filter.

This summary is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1:
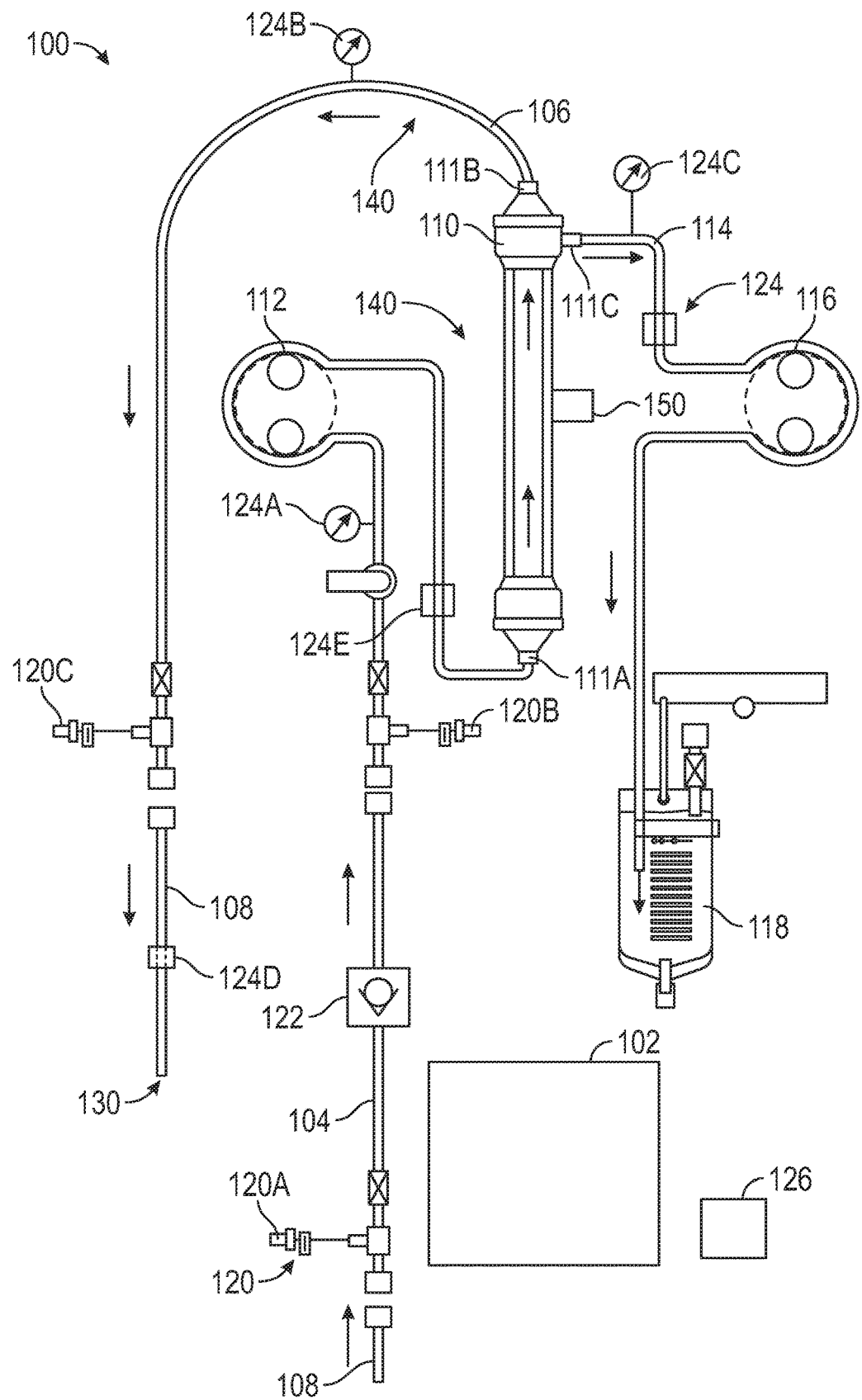
FIG. 1 shows a schematic view of an example of a first blood filtration system.

FIG. 1 shows a schematic view of an example of a first blood filtration system 100. The blood filtration system 100 can be configured to reduce one or more plasma constituents (e.g., water, proteins, electrolytes, or the like) in blood of a patient. The blood filtration system 100 can include a controller 102. The controller 102 can include processing circuitry, for instance an integrated circuit. As described herein, the controller 102 can be configured to control one or more components of the blood filtrations system 100.

The blood filtration system 100 can include a withdrawal line 104 and can include an infusion line 106. The lines 104, 106 can be configured to couple with a catheter 108, and the lines 104, 106 can transmit blood within the blood filtration system 100. In an example, the catheter 108 can be inserted into a blood stream of the patient, for instance the catheter 108 can be inserted into a basilic vein, cephalic vein, brachial vein, the axillary vein, the subclavian vein, the brachiocephalic vein, or the like. Blood can flow into the catheter 108, into the withdrawal line 104, through other components of the system 100, through the infusion line 106, into the catheter 108, and back into the blood stream of the patient. The line 104 can be separate from the line 106. The lines 104, 106 can be in communication with the catheter 108. For example, the catheter 108 can include one or more lumens, for example a withdrawal lumen in communication with the line 104 and an infusion lumen in communication with the line 106.

The lines 104, 106 can be configured to couple with a filter 110, for instance the lines 104, 106 can include one or more fittings that facilitate coupling the lines 104, 106 with the filter 110. In an example, the withdrawal line 104 can couple with a filter inlet port 111A, and the infusion line 106 can couple with a filter outlet port 111B. The filter 110 can be configured to reduce an amount of one or more plasma constituents (e.g., water, electrolytes, or the like) in blood flowing through the filter 110 and provide a filtrate fluid including the one or more plasma constituents. As described herein, blood can flow through the lines 104, 106 to and from the catheter 108. The lines 104, 106 can be coupled with the filter and blood can flow from the withdrawal line 104, through the filter 110, and into the infusion line 106.

The blood filtration system can include a blood pump 112, and the blood pump 112 can be configured to pump (e.g., convey, drive, push, or the like) blood through the blood filtration system 100. In an example, the blood pump 112 can be a peristaltic pump, and the blood pump 112 can engage with the withdrawal line 104 to pump blood through the withdrawal line 104 and into the filter 110. The controller 102 can be configured to operate the blood pump 112 to vary a speed of the blood pump 112 and accordingly vary the flow rate of blood through the blood filtration system 100 (e.g., the withdrawal line 104, the filter 110, the infusion line 106, or the like).

Referring again to FIG. 1, the blood filtration system 100 can include a filtration line 114 and a filtration pump 116. The filtration line 114 can be configured to couple with the filter 110 (e.g., with a fitting), for instance the filtration line 114 can couple with a filtrate fluid port 111C. The filter 110 can be configured to transmit the filtrate fluid (including one or more plasma constituents) to extracted by the filter 110 to the filtrate fluid port 111C.

The filtration pump 116 can pump extracted filtrate fluid from the filter 110, and into a filtrate fluid reservoir 118 (e.g., a bag, container, bladder, or the like). In some examples, the filtration pump 116 can be a peristaltic pump that engages with the filtration line 114 to pump the filtrate fluid through the filtrate fluid line 114. The controller 102 can be configured to vary a speed of the filtration pump 116 and accordingly vary the flow rate of filtrate fluid through the blood filtrate system 100 (e.g., the filtration line 114).

In some examples, the blood filtration system 100 can include one or more access ports 120, for instance a first access port 120A, a second access port 120B, and a third access port 120C. The access ports 120 can facilitate the extraction of blood from the blood filtration system 100, or injection of substances (e.g., a blood thinner, for instance heparin or the like) into the blood within the blood filtration system 100. In an example, the access ports 120A, 120B can be in communication with the withdrawal line 104, and the access port 120C can be in communication with the infusion line 106.

A valve 122 (e.g., a mechanical check valve, or electronically controlled valve) can be positioned between the access ports 120A, 120B, and the valves 122 can be configured to allow blood to flow unidirectionally within the withdrawal line 104 (e.g., flowing from the catheter 108 to the filter 110). In this example, a substance can be injected into the withdrawal line 104 at the access port 120B, and blood can be withdrawn from the access port 120A. Because the valve 122 facilitates unidirectional flow within the withdrawal line 104, the blood including the substance will not be withdrawn from the access port 120A, for instance because the access port 120A is upstream of the access port 120B). In an example, heparin can be infused into the access port 120B and blood is drawn from the access port 120A to measure blood clotting time parameters of a patient. Because the blood is drawn from the access port 120A, the withdrawn blood does not include heparin, and the blood clotting time parameter determination is not affected by the heparin injection at the access port 120B. Accordingly, the performance of blood filtration system 100 is thereby improved.

As shown in FIG. 1, the blood filtration system 100 can include one or more sensors 124 (e.g., transducer, accelerometer, or the like), for instance a first sensor 124A, a sensor 124B, and a sensor 124C. The first sensor 124A can determine (e.g., measure, calculate, obtain, provide, or the like) the pressure within the withdrawal line 104, the second sensor 124B can determine the pressure within the infusion line 106, and the third sensor 124C can determine the pressure within the filtration line 114. The sensors 124 can include a fourth sensor 124D (e.g., a position sensor, or the like) and a fifth sensor 124E (e.g., blood flow rate, or the like), and the sensor 124E can determine the blood flow rate through the system 100 (e.g., a component of the blood circuit 140, for example the withdrawal line 104).

The controller 102 can determine a venous pressure of the patient (e.g., a pressure of a vein that is in communication with the catheter 108). As described herein, the controller 102 can operate the blood pump 112 and control the speed of the blood pump 112. In an example, the controller 102 can vary the speed of the blood pump 112, and stop the blood pump 112 so that there is no blood flow through the blood filtration system 100. Accordingly, pressure in the lines 104, 106 can reach equilibrium with the venous pressure of the patient. As described herein, the sensors 124A, 124B can determine the pressure in the lines 104, 106. Accordingly, when the blood pump 112 is stopped, the controller 102 and sensors 124A, 124B can determine the venous pressure of the patient.

In some examples, the controller 102 can provide a notification of the venous pressure of the patient. In an example, the controller 102 can cooperate with a display (e.g., a screen, for instance an LCD display) to display the determined venous pressure of the patient (e.g., providing the determined venous pressure on a display included in a housing for the system 100).

In another example, the controller 102 can determine a pressure differential between the sensors 124A, 124B. The controller 102 can compare the pressure differential to a pressure differential threshold. In this example, if the pressure differential exceeds the pressure differential threshold, the controller 102 can provide a notification. In an example, the withdrawal line 104, can become blocked (e.g., compressed, twisted, or the like, for instance by a patient leaning on the withdrawal line), and the pressure in the withdrawal line 104 can be greater than the pressure of the infusion line 106.

The pressure differential between the lines 104, 106 can exceed a pressure differential threshold, and the controller 102 can provide a notification that the pressure differential threshold has been exceeded. For instance, the controller 102 can provide a signal to a display to display a message that the withdrawal line 104 is blocked. In another example, the controller 102 can provide a signal to an audio device (e.g., a speaker, a buzzer, or the like) to generate an audio signal that notifies a patient (or a healthcare provider) that the withdrawal line is blocked. Accordingly, the patient or a healthcare provider can remedy the blockage of the withdrawal line 104 and restore proper blood flow in the blood filtration system 100.

As described herein, the blood filtration system (e.g., the system 100) can determine the venous pressure of a patient. For example, the sensors 124A, 124B can determine the pressure in the lines 104, 106, and the controller 102 can be in communication with the sensors 124A, 124B to determine the venous pressure of the patient. The blood filtration system 100 can compensate for pressure head (e.g., static pressure head, static head, the pressure exerted by, or the like) in one or more of the lines 104, 106. For example, the controller 102 can compensate for the pressure head in the lines 104, 106 due to gravitational forces due to a change in elevation (e.g., height, distance, offset or the like) between a catheter tip 130 of the catheter 108 and the one or more of the sensors 124A, 124B that determine the pressure in the lines 104, 106. In some approaches, a ruler is used to determine the elevation difference between the catheter tip 130 and the sensors 124A, 124B.

In an example, the catheter tip 130 can have a different elevation than the sensors 124A, 124B. For instance, the catheter tip 130 can be located in vasculature of a limb of a patient (e.g., in a vein in an arm of the patient, or the like), for example to withdraw or infuse blood into the vasculature. The sensors 124A, 124B can include position sensors that determine the elevation where the sensors 124A, 124B are located (e.g., the elevation where the sensors 124A, 124B determines the pressure in the lines 104, 106). The catheter tip 130 can have a different elevation (e.g., as determined by the sensor 123D) than the sensors 124A, 124B. In an example, the patient can be located on a bed and blood filtration system 100 (including the sensors 124A, 124B) can be located at a different elevation (e.g., on a cart, side table, or the like). Accordingly, the system 100 can determine the difference in elevation between the catheter tip 130 and the elevation where the sensors 124A, 124B are located, for example to compensate for pressure head in the lines 104, 106.

The difference in elevation between the sensors 124A, 124B and the catheter tip 130 can affect the pressure determination by the sensors 124A, 124B in the lines 104, 106, for instance due to pressure head in the lines 104, 106. The system 100 can compensate for pressure head in the lines 104, 106 when determining the venous pressure of the patient. For example, the system 100 can include a fourth sensor 124D, for example an accelerometer. The sensor 124D can determine one or more of position, velocity, acceleration, jerk, or the like. The sensor 124D can be coupled to the catheter 108, and the sensor 124D can be remote from the catheter tip 130. The sensor 124D can be communication with the controller 102, and the controller can determine an elevation difference between the catheter tip 130 and other components of the system 100 (e.g., the sensors 124A, 124B) using the sensor 124D. For example, the system 100 can include one or more accelerometers that provide the elevation of components of the system 100 (e.g., the sensors 124A, 124B), and the system 100 can determine elevation difference between components of the system 100 based on differences in gravitational forces measured by the accelerometers.

The controller 102 can compensate for the pressure head in the lines 104, 106 by determining the pressure head in the lines 104, 106 and using the determined head pressure when determining the venous pressure of the patient (e.g., at the catheter tip 130). For example, the catheter tip 130 can be elevated with respect to the sensors 124A, 124B. The sensors 124A, 124B can determine the pressure in the lines 104, 106, and the pressure in the lines 104, 106 can correspond (at least partially) with the venous pressure in the vasculature where the catheter tip 130 is located. The pressure head in the lines 104, 106 due to the difference in elevation between the tip and the sensors 124A, 124B can affect the pressure determination of the sensors 124A, 124B. For instance, when the catheter tip 130 is located at a higher elevation than the sensors 124A, 124B, the pressure head in the lines 104, 106 can cause the sensors 124A, 124B to determine a pressure that is higher than the actual venous pressure at the catheter tip 130 (e.g., because the pressure head increases the pressure above the actual venous pressure due to the elevation difference between components of the system 100). Accordingly, the system 100 can determine the pressure head in the lines 104, 106, and the system 100 can compensate for the pressure head in the lines 104, 106 when determining the venous pressure of the patient (e.g., at the catheter tip 130).

The blood filtration system 100 can determine density of blood in the vasculature of the patient, for example to improve the accuracy of the pressure head determination. For example, the pressure head in the lines 104, 106 can be determined using the density of blood multiplied by the standard gravity (e.g., 9.8 meters per second-squared) and multiplied by the elevation difference between the sensors 124A, 124B. Accordingly, the density of blood can affect the determination of the pressure head in the lines 104, 106 by the controller 102.

The controller 102 can determine the density of blood in the vasculature of the patient, for example to improve the pressure head determination for the lines 104, 106. In an example, the density of the blood can be determined using a hematocrit value of the blood of the patient (e.g., as determined by the hematocrit sensor 126). Accordingly, the pressure head determination by the controller 102 can be improved using density of the blood.

The system 100 can include a blood circuit 140, and the blood circuit 140 can include one or more components of the system 100. For example, the blood circuit 140 can include (but is not limited to) the withdrawal line 104, the infusion line 106, the catheter 108, the filter 110, the filtration line 114, the filtrate fluid reservoir 118. The blood circuit 140 can include components of the system that are in communication with a biological fluid of the patient.

The system 100 can include an activation key 150, and the activation key 150 can be in communication with the controller 102, for example to provide information about the blood circuit 140 to the controller 102. The activation key 150 can include (but is not limited to) an electronic device (e.g., a radio frequency identification tag, memory card, or the like) that interconnects with the system 100 (e.g., wirelessly, or with wires, interconnects, or the like), For example, the activation key 150 can include a radio frequency identification tag, and the system 100 can communicate with the activation key when the blood circuit 140 is located proximate to the system 100. The activation key 150 can store information provided by the system 100, for example usage information related to the blood circuit 140.

In an example, the activation key 150 can be coupled with a portion of the blood circuit 140 (e.g., the activation key 150 can be coupled with the filter 110). The activation key 150 can be unique to (e.g., paired with, tied to, associated with, or the like) an individual one of the blood circuit 140 to provide information to the system 100 about the individual one of the blood circuit 140. For example, the activation key 150 can provide the controller 102 with circuit characteristics of the blood circuit 140. The circuit characteristics can include (but are not limited to) dimensions (e.g., size, length, diameter, or the like) of the lines 104, 106; dimensions of the filter 110; types of filters (e.g., a first filter intended for use with a child or a second filter intended for use with an adult, or the like); dimensions of the catheter 108; or the like.

In some examples, the controller 102 can evaluate the circuit characteristics provided by the activation key 150 to operate the system 100 at a configuration specific to the circuit characteristics of the blood circuit 140 coupled to the system 100. In an example, a first blood circuit 140 can include a first filter 110 (e.g., a small filter) and a first activation key 150 that includes a first set of circuit characteristics (e.g., that correspond to a small filter). A second blood circuit 140 can include a second filter 110, and the second filter 110 (e.g., a large filter) can include a second set of circuit characteristics (e.g., that correspond to a large filter). The system 100 can determine whether the first blood circuit 140 or the second blood circuit 140 are coupled with the system 100, for example by evaluating the circuit characteristics stored by the activation key 150. The controller 102 can operate the system 100 according to the first set of circuit characteristics, for example by operating the blood pump 112 at a first blood flow rate. The controller 102 can operate the system 100 according to the second set of circuit characteristics, for instance by operating the blood pump 112 at a second blood flow rate. Operating the system 100 in correspondence with the circuit parameters provided by the activation key 150 can improve patient safety, for example by limiting the rate that blood is withdrawn from a patient (e.g., where the blood circuit 140 is used with a pediatric patient that requires a reduced blood flow rate in comparison to the blood flow rate for an adult patient).

As described herein, the activation key 150 can be in communication with the controller 102. The controller 102 can provide the activation key 150 with an activated characteristic, for example when the blood circuit 140 is connected with other components of the system 100 (e.g., the blood pump 112). The activated characteristic can indicate whether the blood circuit 140 has been previously used with the system 100. Providing the activated characteristic to the activation key 150 can inhibit the reuse of the blood circuit 140, for example to inhibit (e.g., stop, prevent, block, or the like) the use of the blood circuit 140 (or individual components of the blood circuit 140) with more than one patient. In another example, the system 100 can limit the time duration that an individual one of the blood circuit 140 can be used with the system 100 (e.g., to limit the time that the filter 110 can be used in renal replacement therapy).

The activation key 150 can store the activated characteristic when the activated characteristic is provided by the controller 102. For example, the activation key 150 can include memory, and the activation key 150 can store data corresponding to the activated characteristic in the memory (e.g., a solid state memory device, or the like). The system 100 can read the activated characteristic stored by the activation key 150, for example to determine whether the blood circuit 140 was previously coupled with the system 100 (e.g., to inhibit more than one use of the blood circuit 140).

When the system 100 (e.g., the controller 102) determines whether the blood circuit 140 was previously coupled with the system 100, the system 100 can inhibit operation of the system 100 (e.g., by inhibiting one or more functions of the system 100. For example, the controller 102 can inhibit operation of the blood pump 112 to inhibit the system 100 from withdrawing blood from the patient. In another example, the system 100 can provide a notification (e.g., by displaying a message on a display, for example an LCD screen, or the like) that the blood circuit 140 with an activated characteristic has been coupled with the system 100.

As described herein, the system 100 can limit the time duration that an individual one of the blood circuit 140 can be used with the system 100. For example, the system 100 can limit a usage time that the blood circuit 140 is used with the system 100. In an example, the controller 102 can provide the activation key 150 with an expiration characteristic. The controller 102 can provide the expiration characteristic after a specified time period (e.g., 12 hours, 2 days, 3 days, or the like) from when the controller 102 provided the activated characteristic to the activation key 150. The activation key 150 can store one or more usage characteristics of the blood circuit 140. For example, the activation key 150 can store the usage time that the blood circuit 140 has been used during therapy with the system 100. In some examples, the system 100 can provide a notification (e.g., by transmitting a message to a mobile device, or the like) that the usage time of the blood circuit 140 is approaching the specified time period where the system 100 will inhibit the use of the blood circuit 140 with the system 100 (e.g., by providing the expiration characteristic to the activation key 150). The notification can notify a health provider to change (e.g., swap, or the like) the used blood circuit 140 with a new blood circuit 140 (e.g., when the usage time reaches 80 percent of the specified time period).

FIG. 1 shows the blood filtration system 100 can include a hematocrit sensor 126. In some examples, the hematocrit sensor 126 can include an optical hematocrit sensor, and the hematocrit sensor 126 can be coupled with one or more of the lines 104, 106, and the hematocrit sensor 126 can determine a hematocrit value (e.g., level, or the like) of the patient. In an example, the hematocrit sensor 126 can be located between the catheter 108 and the valve 122, for instance to monitor the hematocrit value of the patient prior to injection of a fluid (e.g., heparin or saline) into the blood (e.g., at the access port 120B). Accordingly, the hematocrit value determination can be improved with the system 100.

In an example, the controller 102 can be configured to control the speed of the blood pump 112 and set the flow rate of blood through the filter 110 at a first blood flow rate. Additionally, the controller 102 can be configured to control the speed of the blood pump 112 and set the flow rate of blood through the filter at a second blood flow rate. The first blood flow rate can be different than the second blood flow rate. The controller 102 can determine the hematocrit at the second blood flow rate. The controller 102. can control the speed of the blood pump 112 and set the flow rate of blood at the first blood flow rate after determining the hematocrit value, for example after determining the hematocrit value at the second blood flow rate.

The controller 102 can control the speed of the blood pump 112 to measure the hematocrit value because the hematocrit value can vary according to the speed of the blood pump 112, and controlling the speed of the blood pump can improve the accuracy of the hematocrit value determination. For instance, the hematocrit value determination by the hematocrit sensor 126 can be affected by the flow rate of blood through the filter. In this example, the speed of the blood pump 112 can vary, and the determined hematocrit value of the patient can vary according to the speed of the blood pump 112. Accordingly, measuring the hematocrit value with the blood pump 112 at a consistent speed can improve the accuracy of the hematocrit value determination. Accordingly, varying the speed of the blood pump 112 can account for a source of error in determining the hematocrit value and the performance of the blood filtration system 100 is thereby improved.

As described herein, the blood filtration system 100 can determine a hematocrit value of a patient. The hematocrit value of the patient can be defined by Equation (1): H=RBCV/BV, where H is the hematocrit value, RBCV is the red blood cell volume, and BV is the total blood volume (e.g., the RBCV plus plasma volume). Equation (1) can be rearranged to determine the red blood cell volume, as shown in Equation (2): BV=RBCV/H. The derivative of Equation (2) is shown in Equation (3):

$$\frac{d(BV)}{dt} = RBCV * \frac{d\left(\frac{1}{H}\right)}{dt}$$

where 1/H is an inverse of the hematocrit value. The change of blood volume for a patient undergoing blood filtration with the blood filtration system 200 is shown in Equation (4):

$$\frac{d(BV)}{dt} = PRR - FR$$

where PRR is the plasma refill rate, and FR is the filtration rate (e.g., the rate of filtrate fluid flowing from the filter 110). The plasma refill rate is the rate that the plasma volume changes with respect to time, from within the body of the patient (e.g., the flowing of plasma water into the blood stream from interstitial spaces of the body into the venous system of the patient).

The filtration rate can be varied (e.g., changed), for instance by varying the speed of the filtration pump 116, and the change in filtration rate is shown in Equation (5):

$$\Delta FR = FR_2 - FR_1$$

Combining Equations (3) and (4) yields Equation (6):

$$PRR - FR = RBCV * \frac{d\left(\frac{1}{H}\right)}{dt}$$

As described herein the filtration rate (FR) can be varied, and accordingly substituting Equation (6) into Equation (5), and performing additional algebra yields Equation (7):

$$RBCV = \frac{\Delta FR}{\frac{d\left(\frac{1}{H2}\right)}{dt} - \frac{d\left(\frac{1}{H1}\right)}{dt}}$$

where $H_1$ is the hematocrit value at the first filtration rate $(FR_1)$, and $H_2$ is the hematocrit value at the second filtration rate $(FR_2)$. The controller 102 can be configured to determine a red blood cell volume using Equation (7).

Substituting Equation (7) into Equation (1) yields Equation (8).

$$BV(\text{at } t = tx) = \frac{RBCV}{H_{t=tx}}$$

Performing algebraic manipulation of Equation (8) yields Equation (9):

$$PV(\text{at } t = tx) = RBCV \times \left(\left(\frac{1}{Hx}\right) - 1\right)$$

where PV is the plasma volume of the patient.

The controller 102 can use Equation (9) to determine the plasma volume of the patient, and determine when to stop filtering the blood of the patient. In another example, the red blood cell volume can be determined using Equation (10):

$$RBCV = (FV) * \frac{Hfinal * Hinit}{Hfinal - Hinit}$$

where FY is the volume of filtrate fluid extracted from the patient (e.g., by the filtration pump 116), $H_{init}$ is the hematocrit value at the beginning of filtration therapy (e.g., when the filtration pump 116 is started), and $H_{final}$ is the hematocrit value at the end of filtration therapy (e.g., when the filtration pump 116 is stopped). $H_{init}$ and $H_{final}$ can be determined using the hematocrit sensor 126

Determining the red blood cell volume with the blood filtration system 100 can reduce the need to determine the red blood cell volume with other methodologies. For instance, a tracer (e.g., a radioactive tracer, cardiac green, or saline, or the like) can be injected into a blood stream of the patient. One or more blood samples can be withdrawn from the patient to determine the red blood cell volume. The red blood cell volume can be used to determine the quantity of the one or more plasma constituents to extract from the patient. In this example, the red blood cell can be inputted into the blood filtration system, for instance at the beginning of therapy. In another example, the controller 102 can determine the red blood cell volume according to Equation (7) or Equation (10). In some examples, the controller 102 is optionally configured to set an extraction rate of filtrate fluid from the filter 110 using the determined red blood cell volume or the determined hematocrit value of the patient.

As described herein, the plasma refill rate is the rate that the plasma volume changes with respect to time, from within the body of the patient (e.g., the flowing of plasma water into the blood stream from interstitial spaces of the body). The plasma refill rate can affect the plasma volume determination, for instance when using Equation (9). The plasma refill rate can be determined using Equation (11):

$$PRR = \frac{FV * [H1 * H2 - H1 * H3]}{\tau 1 * [H1 * H2 - H1 * H3] - \tau 2 * [H1 * H3 - H2 * H3]}$$

where FV is the volume of filtrate fluid extracted from the patient (e.g., by the filtration pump 116), H1 is a first hematocrit value determination, H2 is a second hematocrit value determination, H3 is a second hematocrit value determination, π1 is the time difference between the H1 and H2 determinations, and π2 is the time difference between the H2 and H3 determinations. H1 can be determined at the beginning of filtration therapy (e.g., when the filtration pump 116 is started). H2 can be determined at the end of filtration therapy (e.g., when the filtration pump 116 is stopped). H3 can be determined after a waiting period (e.g., one hour) where the blood pump is operated (e.g., turned on), while the filtration pump 116 is not operated (e.g., turned off). Accordingly, the blood filtration system 100 can determine the plasma refill rate and use the plasma refill rate to determine when to stop therapy of the patient, and when the patient has reached euvolemia. The controller 102 can use one or more of Equations (1)-(11) during therapy to determine a quantity of filtrate fluid to extract from the patient, and determine how much plasma remains in the patient at a given point in time. Accordingly, the controller 102 using one or more of Equations (1)-(11) (or Equations (1)-(17)) can improve the performance of the blood filtration system (e.g., the system 100).

As described herein, Equation (1) is H=RBCV/BV, where H is the hematocrit value, RBCV is the red blood cell volume, and BV is the total blood volume. Equation (1) can be equivalent to: H=RBCV/(RBCV+PV), where PV is the plasma volume. Equation (12) facilitates the determination of the density of the blood of the patient (e.g., whole blood, unfiltered blood, or the like):

$$\rho_b = \frac{mass}{volume} = \frac{\rho_r * RBCV + \rho_p * PV}{RBCV + PV}$$

where $\rho_b$ is the density of the blood of the patient, $\rho_r$ is the density of a single blood cell, $\rho_p$ is the density of plasma, PV is the plasma volume. In an example, the system 100 can determine one or more of the hematocrit value, the density of plasma $\rho_p$, and the density of a single blood cell $\rho_r$. For example, the system can determine the hematocrit value H, the density of plasma $\rho_p$, or the density of a single blood cell $\rho_r$ using one or more equations or constants, including (but not limited to) Equations (1)-(17). Performing one or more mathematical operations on Equation (1) yields Equation (13):

$$(H-1)*RBCV+H*PV=0$$

Performing one or more mathematical operations on Equation (12) yields Equation (14):

$$(\rho_b-\rho_r)*RBCV+(\rho_b-\rho_p)*PV=0$$

Performing one or more mathematical operations on Equations (13) and (14), for example by simultaneously solving Equations (13) and (14) yields Equation (15):

$$H = \frac{\rho_b - \rho_p}{\rho_r - \rho_p}$$

The density of blood of the patient $\rho_b$ can be determined using Equation (15), for example by performing one or more mathematical operations on Equation (15) to yield Equation (16):

$$\rho_b=\rho_p*(1-H)+H*\rho_r$$

Accordingly, the system 100 can determine the density of blood of the patient $\rho_b$ using the hematocrit value H determination.

FIG. 1 shows the withdrawal line 104 in communication with the sensor 124A and the infusion line in communication with the sensor 124B. As described herein, the sensors 124A can determine pressure in the withdrawal line 104, and the sensor 124B can measure pressure in the infusion line 106. The sensors 124A, 124B can be in communication with the controller 102, and the controller 102 can determine the pressure in the lines 104, 106 using the sensors 124A, 124B.

When the controller 102 operates the blood pump 112, the blood pump 112 generates a negative pressure in withdrawal line 104 to withdraw blood from the vasculature where the catheter tip 130 is located. The blood pump 112 can generate a positive pressure in the infusion line 106 to infuse blood into the vasculature where the catheter tip 130 is located. The magnitude of the pressure in lines 104, 106 can increase to correspondingly increase the blood flow rate within the lines 104, 106.

The blood circuit 140 (including the lines 104, 106) can have a total resistance characteristic that corresponds to an amount of resistance in the blood circuit 140 to the flow of blood through one or more components of the blood circuit, for instance the lines 104, 106 or the filter 110. One or more characteristics can contribute to the total resistance characteristic of the lines 104, 106. For example, the resistance characteristic of the lines 104, 106 can increase due to occlusion (e.g., clotting, obstruction, or the like) of the blood circuit 140 (e.g., in or around the catheter 108), changes to the vasculature (e.g., inflammation of walls of the vasculature, compression of the vasculature, or the like), hemoconcentration of the blood, or the like. The resistance characteristic (e.g., transverse or longitudinal) of the filter 110 can contribute to the total resistance characteristic of the blood circuit 140.

An increase in the resistance characteristic of the lines 104, 106 (or other components of the blood circuit 140) can diminish blood flow through the lines 104, 106. The diminished blood flow due to the increase in the resistance characteristic of the lines 104, 106 can reduce the performance of the system 100, for example by reducing the maximum blood flow rate through the blood circuit 140 or the rate that the one or more blood constituents can be removed from the blood by the filter 110. The resistance characteristic of the lines 104, 106 can increase to the point where the blood pump 112 is unable to maintain flow within the lines 104, 106 (e.g., because the forces resisting flow in the lines exceeds the forces generated by the blood pump 112). Accordingly, an increase in the resistance characteristic of the lines 104, 106 can diminish the performance of the blood filtration system 100.

The system 100 can determine a total resistance characteristic for one or more components of the blood circuit 140, for example the withdrawal line 104 and the infusion line 106. In an example, a withdrawal line resistance characteristic can correspond to the resistance in the withdrawal line 104 to the flow of blood through the withdrawal line 104. The withdrawal line resistance characteristic can correspond to the pressure in the withdrawal line 104 divided by the actual blood flow rate of system 100 (e.g., as determined by sensor 124E). The actual blood flow rate of the system 100 can vary from a set point that the controller 102 operates the blood pump 112 at. For example, the resistance characteristic of the lines 104, 106 can reduce the actual blood flow rate through the blood circuit 140 because the resistance to the flow of blood in the lines 104, 106 decreases the efficiency of the blood pump 112.

The infusion line resistance characteristic can correspond to the resistance in the infusion line 106 to the flow of blood through the infusion line 106. The infusion line resistance characteristic can correspond to the pressure in the infusion line 106 divided by the difference between the actual blood flow rate and the filtration rate of the system (e.g., as determined by controller 102 in communication with the sensors 124). An increase in the magnitude of the resistance characteristic of the blood circuit 140 (including the lines 104, 106) can increase the force necessary to withdraw blood from (or infuse blood into) the patient by the blood pump 112. The increase in the magnitude of the resistance characteristic of the blood circuit 140 can result in (or be an indication of) clotting in the blood circuit 140.

The hematocrit value of the patient can contribute to the total resistance characteristic of the blood circuit 140. As described herein, the blood filtration system 100 can determine the hematocrit value of the patient. Hemoconcentration (e.g., an increase in the hematocrit) of the blood of the patient can increase the density or viscosity of the blood. Accordingly, an increase in hematocrit of the patient can increase the resistance of blood to flow in the blood circuit 140. The system 100 can determine a hemoconcentration resistance characteristic using the determined hematocrit value of the patient (or a determined venous pressure of the patient). The hemoconcentration resistance characteristic can correspond to the resistance to the flow of the blood of the patient through the blood circuit 140.

In an example, the total resistance characteristic of the lines 104, 106 can increase due to occlusion (e.g., clotting, obstruction, or the like) of the blood circuit 140, changes to the vasculature, hemoconcentration of the blood, or the like. The system 100 can determine an occlusion resistance characteristic of the lines 104, 106. The occlusion resistance characteristic can correspond to the resistance of the flow of blood through the lines 104, 106 due to an occlusion of the circuit or changes in vasculature of the patient. The occlusion resistance characteristic can correspond to the difference between the withdrawal line resistance characteristic and the hemoconcentration resistance characteristic. The occlusion resistance characteristic can correspond to the difference (e.g., by performing a subtraction mathematical operation) between the infusion line resistance characteristic and the hemoconcentration resistance characteristic. Accordingly, the system 100 can determine what resistance characteristics (e.g., the hemoconcentration resistance characteristic, or the like) are contributing to the total resistance characteristic for the blood circuit 140 (including the lines 104, 106).

The system 100 can provide a notification of one or more of the resistance characteristics that are determined by the system 100. For example, the system 100 can provide a notification on a display of the withdrawal line resistance characteristic or the infusion line resistance characteristic. In another example, the system 100 can provide a notification of the occlusion resistance characteristic to inform a user (e.g., a healthcare provider, or the like) that resistance in the blood circuit 140 is due to an occlusion or the changes in vasculature of the patient. For example, the notification of the occlusion resistance characteristic can allow a user to apply appropriate corrective measures to increase the lifetime of the blood circuit 140. In an example, the user can inject an anticoagulant to try and reduce clotting in the blood circuit 140. In another example, the user can manipulate the catheter 108 to reposition the catheter tip 130 relative to the vasculature of the patient (e.g., to move the catheter tip 130 away from a wall of the vasculature).

In some examples, the system 100 provides a notification of pressures in the blood circuit 140 (e.g., pressure in the withdrawal line 104). The pressure in the withdrawal line 104 can be indicative of the total resistance characteristic of the blood circuit. However, as described herein, the total resistance characteristic depends upon other characteristics (e.g., variables, or the like), including (but not limited to) the occlusion resistance characteristic and the hemoconcentration resistance characteristic. Determining the occlusion resistance characteristic and the hemoconcentration resistance characteristic can facilitate diagnosis for the cause of an increase in the total resistance characteristic of the blood circuit 140. Diagnosing the cause of the increase in the total resistance characteristic of the blood circuit 140 can facilitate appropriate corrective measures to reduce the total resistance characteristic of the blood circuit 140. Accordingly, the system 100 can improve the lifetime of the blood circuit 140, for example by reducing replacement of components of the blood circuit 140 (e.g., the filter 112) due to clotting.

Figure 2:
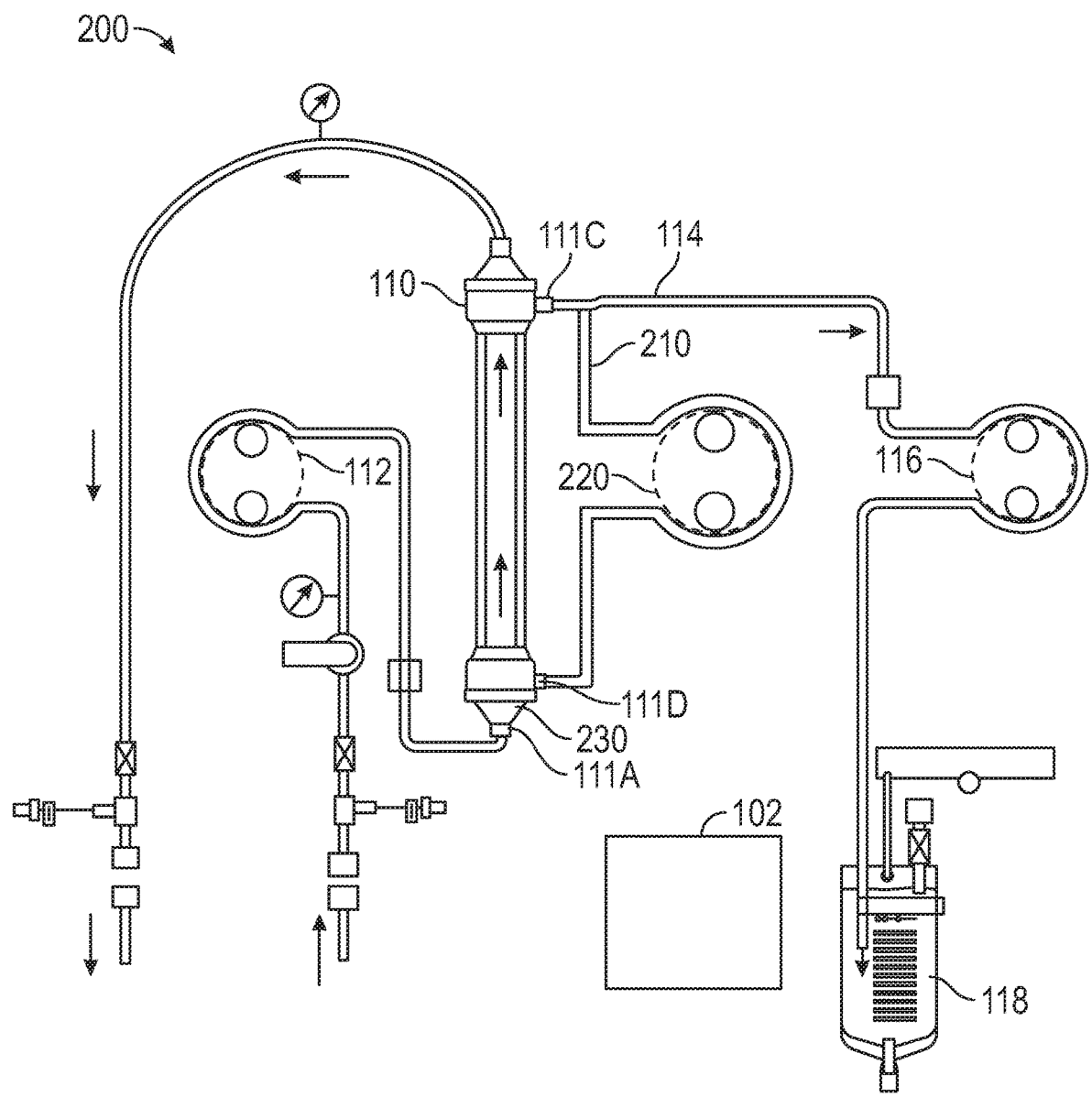
FIG. 2 shows a schematic view of an example of a second blood filtration system.

FIG. 2 shows a schematic view of an example of a second blood filtration system 200. The blood filtration system 200 can include, but is not limited to, the blood pump 112, the filter 110, the filtration line 114, and the filtration pump 116. Additionally, the filtration system 200 can include a harvest fluid line 210, and can include a harvesting pump 220. The harvest fluid line 210 can be in communication with the filtrate fluid port 111C, for example, the harvest fluid line 210 can be coupled to the filtration line 114, and the harvest fluid line 210 can receive filtrate fluid from the filtration line 114.

In some examples, the filter 110 includes a harvesting port 111D. The harvesting port 111D can be configured to receive filtrate fluid. In an example, the harvest fluid line 210 is coupled with the harvesting port 111D, and the harvesting port 111D is in communication with the filtrate fluid port 111C through the harvest fluid line 210. The harvesting pump 220 can engage with the harvest fluid line 210 and pump filtrate fluid from the filtrate fluid port 111C to the harvesting port 111D. The controller 102 can operate (e.g., activate, turn on, energize, provide a control signal to, or the like) the harvesting pump 220 to extract filtrate fluid from a filtrate reservoir (e.g., the filtrate fluid port 111C, the filtration line 114, or the filtrate fluid reservoir 118) and inject the filtrate fluid into the harvesting port 111D to dilute the blood flowing through the filter.

In some examples, the harvesting port 111D is included in (e.g., extends from, or is in communication with) a filter body 230 of the filter 110. In another example, the harvesting port 111D is coupled with the blood inlet port 111A. Optionally, a one-way valve is included between the filtrate fluid port 111C and the harvesting port 111D, for instance to inhibit blood flow within the harvest fluid line 210 while allowing filtrate fluid to flow from the filtrate fluid port 111C to the harvesting port 111D. As described in greater detail herein, the harvesting port 111D can provide filtrate fluid into the filter to dilute blood within the filter and inhibit clotting of blood flowing through the filter.

Figure 3:
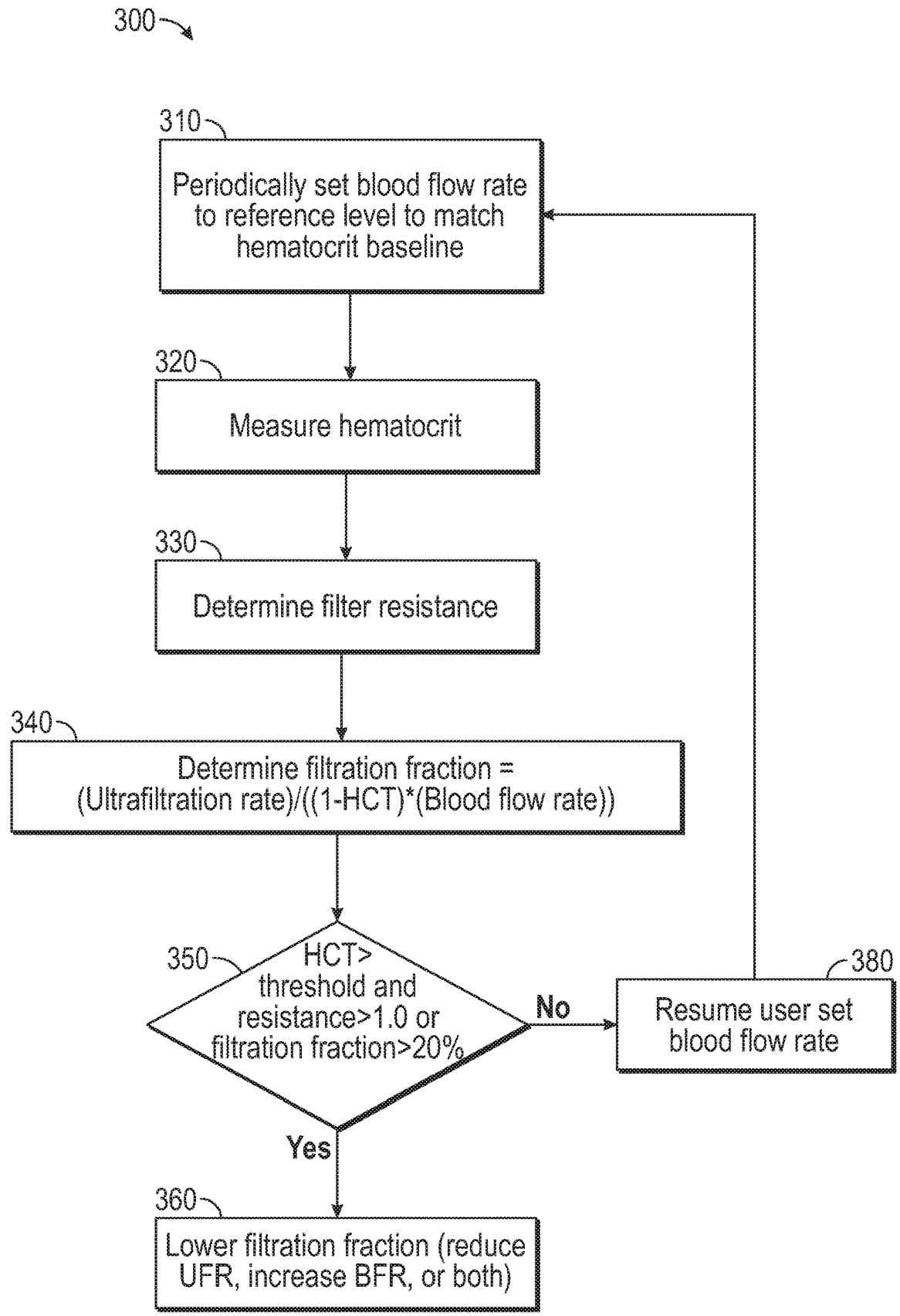
FIG. 3 shows a flowchart of a first method for preserving a filter for a blood filtration system.

FIG. 3 shows a flowchart of a first method 300 for preserving a filter for a blood filtration system (e.g., the blood filtration system 100 or the blood filtration system 200). In describing the method 300, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 300 include, but are not limited to, the corresponding numbered elements provided herein and other corresponding elements described herein (both numbered and unnumbered) as well as their equivalents. Additionally, the method 300 can be included in instructions on a computer readable medium, and the instructions can be carried out by the controller 102 (e.g., processing circuitry).

At operation 310 the blood flow rate can be periodically set to a reference level (e.g., operating the blood pump 112 at the second blood flow rate). At operation 320 the hematocrit value of the patient can be determined (e.g., with the hematocrit sensor 126 shown in FIG. 1). A filter resistance of the filter 110 can be determined at operation 330. In an example, the filter resistance can be determined by determining a pressure differential between the sensors 124A, 124B (shown in FIG. 1). The filter resistance can be determined with the blood pump operating, for instance at the second blood flow rate. At operation 340, a filtration fraction can be determined according to Equation (17):

$$\text{Filtration Fraction} = \frac{\text{Filtration Flow Rate}}{(1 - \text{Hematocrit Value})(\text{Blood Flow Rate})}$$

At operation 350, the hematocrit value is compared to a hematocrit threshold (e.g., 0.50) and if the hematocrit value is greater than the hematocrit threshold, or if the filtration fraction is greater than a filtration fraction threshold (e.g., 0.20), the filtration fraction can be reduced at operation 360. Reducing the filtration fraction can be reduced, for instance, by the controller 102. The controller 102 can be configured to control a speed of one or more pumps to adjust the filtration fraction of the system. The controller can vary the speed of the one or more pumps (e.g., the filtration pump 116, the blood pump 112, or the like) to adjust the filtration fraction Controlling the filtration fraction can be used to control the rate of removing plasma constituents while maintaining preferred patient diagnostic parameters.

Additionally, controlling the filtration fraction can be used to reduce clogging of the extracorporeal components of a blood filtration system (e.g., the blood filtration system 100, or the blood filtration system 200). In this example, if the hematocrit value is less than the hematocrit threshold, or if the filtration fraction is less than a filtration fraction threshold (e.g., 0.20), the blood flow rate of the system can be set to a user set blood flow rate (e.g., operating the blood pump 112 at the first blood flow rate).

Figure 4A:
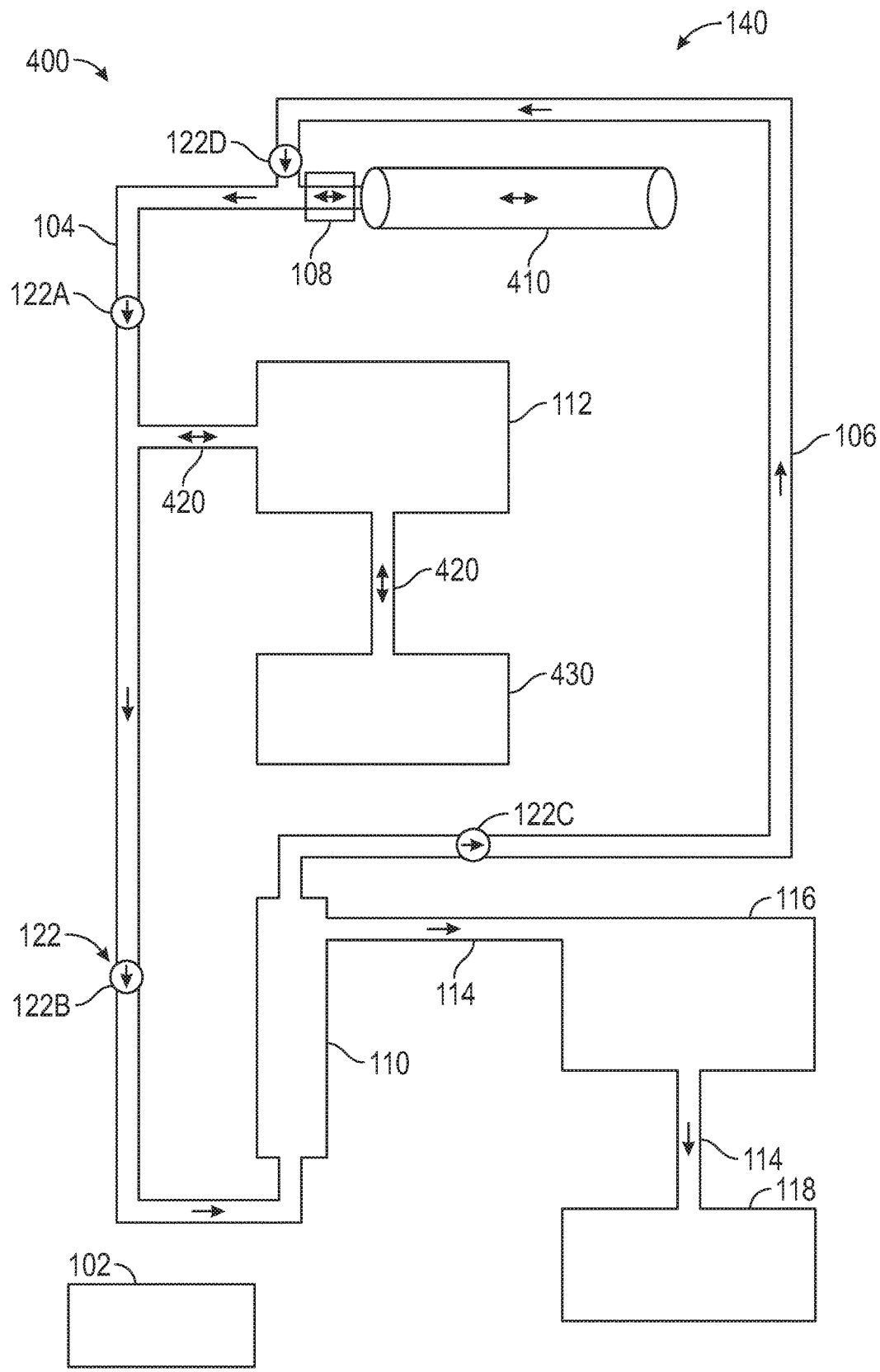
FIGS. 4A-4H show a schematic view of an example of a third blood filtration system.

FIGS. 4A-4H show a schematic view of an example of a third blood filtration system 400. As shown in FIG. 4A, the filtration system 400 can include the controller 102, the withdrawal line 104, the infusion line 106, the catheter 108, the filter 110, the blood pump 112, the filtration line 114, the filtration pump 116, the filtration fluid reservoir 118, and the one or more valves 122. The valves 122 can include a check valve, pinch valve (e.g., a valve that pinches a portion of the blood circuit 140, for instance the lines 104, 106), electro-mechanical valve, or the like. The catheter 108 can be inserted into vasculature 410 of a patient (e.g., a central venous system, peripheral venous system, basilic vein, cephalic vein, brachial vein, the axillary vein, the subclavian vein, the brachiocephalic vein, or the like). The blood pump 112 can be in communication with a blood reservoir 430. In an example, the withdrawal line 104 can be in communication with a blood reservoir line 420. The controller 102 can be configured to control the blood pump 112 to operate the blood pump 112 in a first flow direction to transmit blood from the patient into the blood reservoir.

Additionally, the controller 102 can be configured to control the blood pump 112 to transmit blood from the blood reservoir 430 to the filter 110. For instance, the blood pump 112 can be controlled to operate the blood pump 112 in a second flow direction. The second flow direction can be opposite to the first flow direction. As described herein, the blood filtration system 400 can include the one or more check valves 122, for instance a first valve 122A, a second valve 122B, a third valve 122C, and a fourth valve 122B. The first valve 122A can allow for unidirectional flow within the withdrawal line 104 and prevent blood from being transmitted into the catheter 108 when the blood pump 112 is operated in the second flow direction. Accordingly, the valve 122A facilitates transmission of blood from the blood reservoir 430 to the filter 110.

In some examples, the valves 122 are operated out of phase with each other. For instance, the controller 122A can operate the valve 122A to permit flow through the withdrawal line 104. The controller 102 can operate the valve 122D to inhibit flow through the infusion line 106. Accordingly, the controller 102 can operate the valve 122A out of phase with the valve 122D. Inhibiting the flow in one or more of the lines 104, 106 can facilitate unidirectional flow through the system 100 (e.g., the blood circuit 140). In an example, operating the valves 122. (e.g., the valves 122A, 122D, or the like) out of phase can inhibit the flow of blood from the infusion line 106 to the withdrawal line (or from the withdrawal line 104 to the infusion line 106). For instance, closing the valve 122D can facilitate withdrawal of blood from the vasculature 410 of the patient while inhibiting flow of blood from the infusion line 106 to the withdrawal line 104. The valve 122A can be operated to facilitate unidirectional flow in the system 400, for example by closing the valve 122A to inhibit flow from the withdrawal line 104 to the infusion line 106 (or from the withdrawal line 104 to the vasculature 410 during infusion of the blood into the vasculature 410. Accordingly, operating the valves 122 out of phase with each other can facilitate unidirectional flow through the system 400 (or other systems described herein, for example the system 100, or the like).

The filtration pump 116 can pump extracted filtrate fluid from the filter 110, and into the filtrate fluid reservoir 118. In some examples, the filtration pump 116 can be a peristaltic pump that engages with the filtration line 114 to pump the filtrate fluid through the filtrate fluid line 114. The controller 102 can be configured to vary a speed of the filtration pump 116 and accordingly vary the flow rate of filtrate fluid through the blood filtrate system 100 (e.g., the filtration line 114).

The system 400 can facilitate the use of a single lumen catheter 108, however the present subject matter is not so limited. For instance, the catheter 108 can include a single passage, and blood can be withdrawn and infused within the single passage. The single lumen catheter facilitates increased blood flow in the system 400. Accordingly, the increased blood flow reduces clogging in the filter 110, thereby improving the performance of the system 400.

Figure 4B:
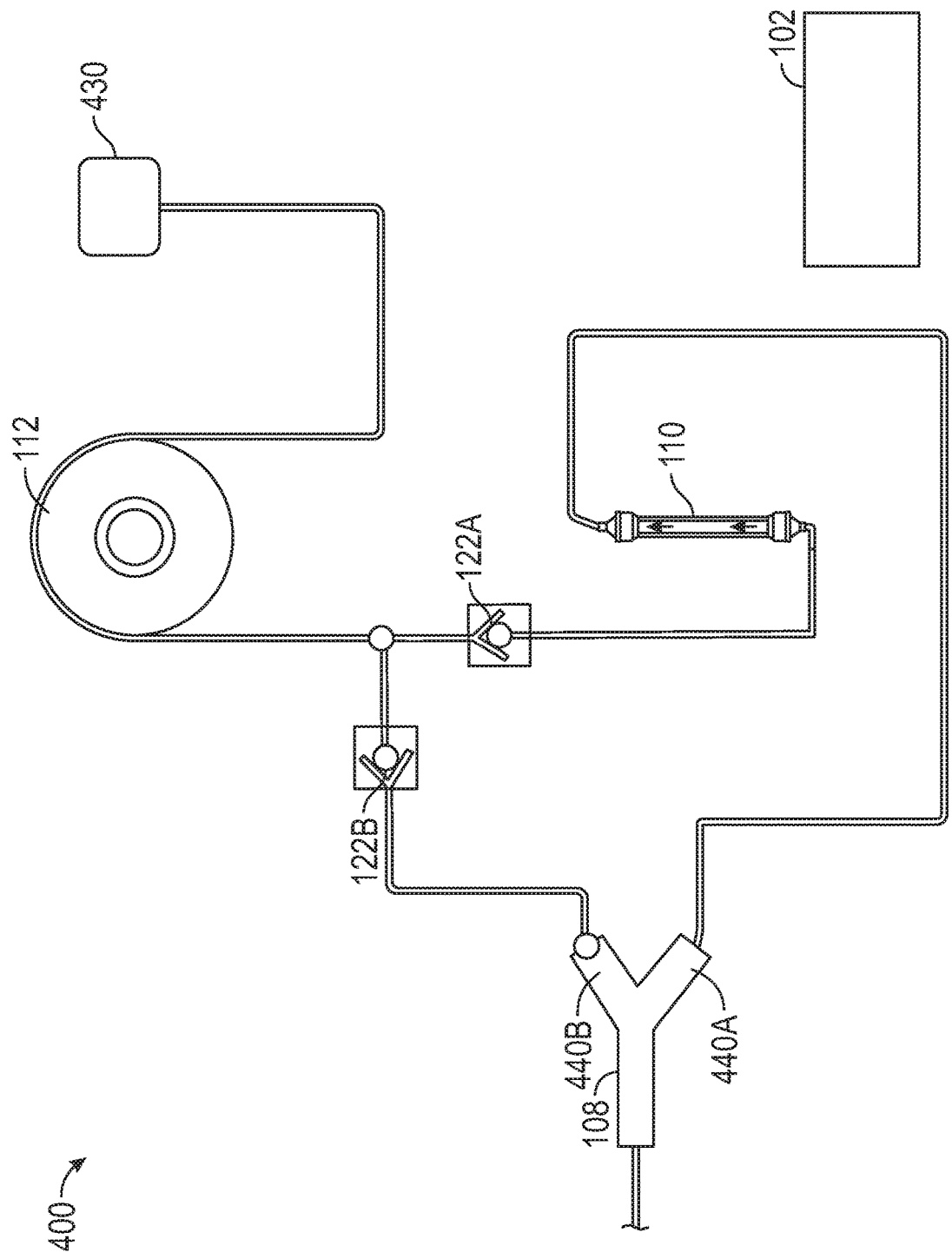
Figure 4C:
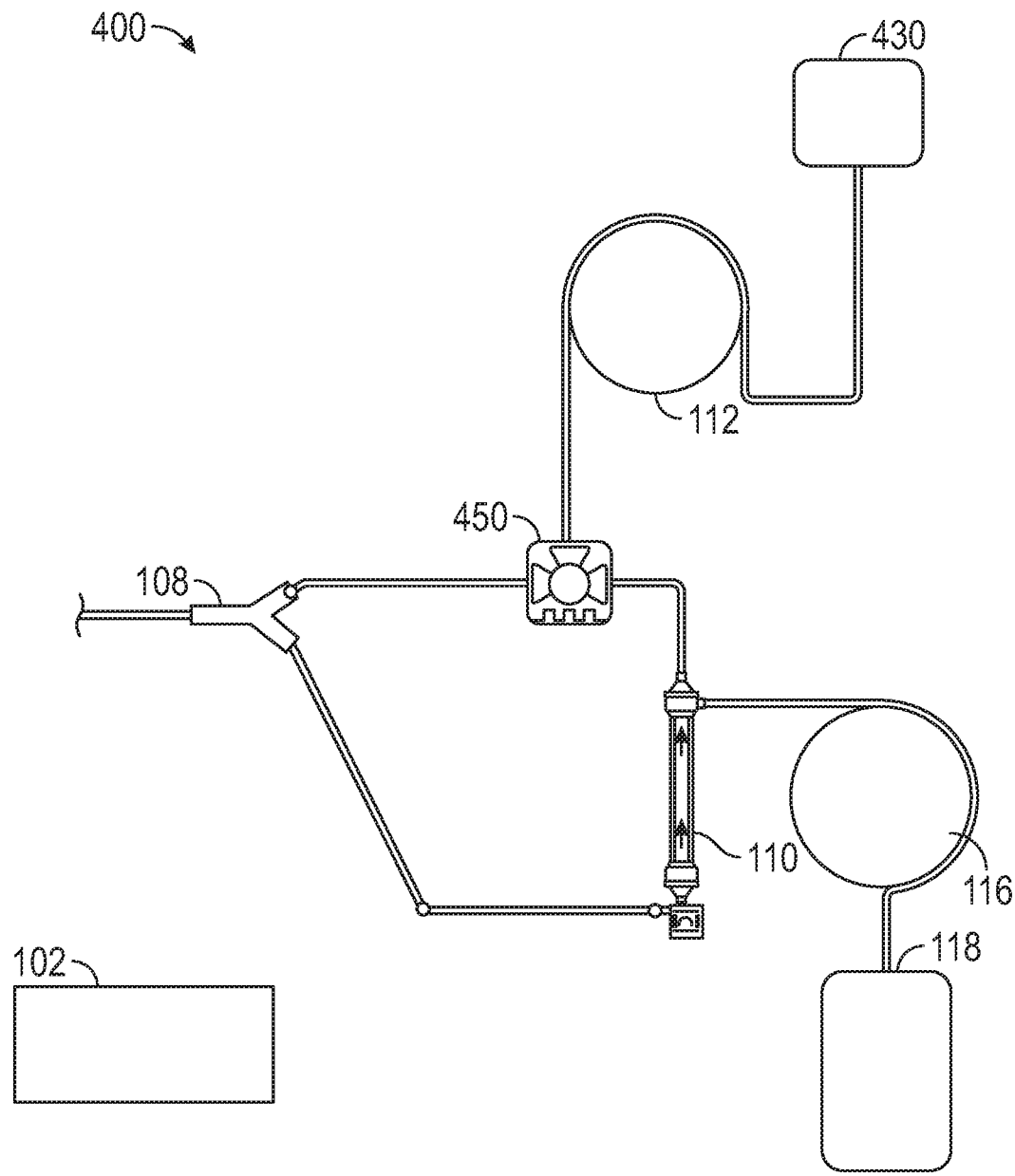

As shown in FIG. 4B, in some examples, the catheter 108 includes a withdrawal port 440A that can be isolated from an infusion port 440B. FIG. 4C shows that the blood filtration system 400 can include a diverter valve 450. The diverter valve 450 can be controlled by the controller 102, for instance the controller 102 can provide a control signal to operate the diverter valve 450. The diverter valve 450 can be operated to allow for blood to flow in one or more directions. In an example, the diverter valve 450 can be operated to allow blood to flow from the catheter 108 to the blood reservoir 430, while preventing blood from being withdrawn from other portions of the blood filtration system 400 (e.g., the filter 110).

Figure 4D:
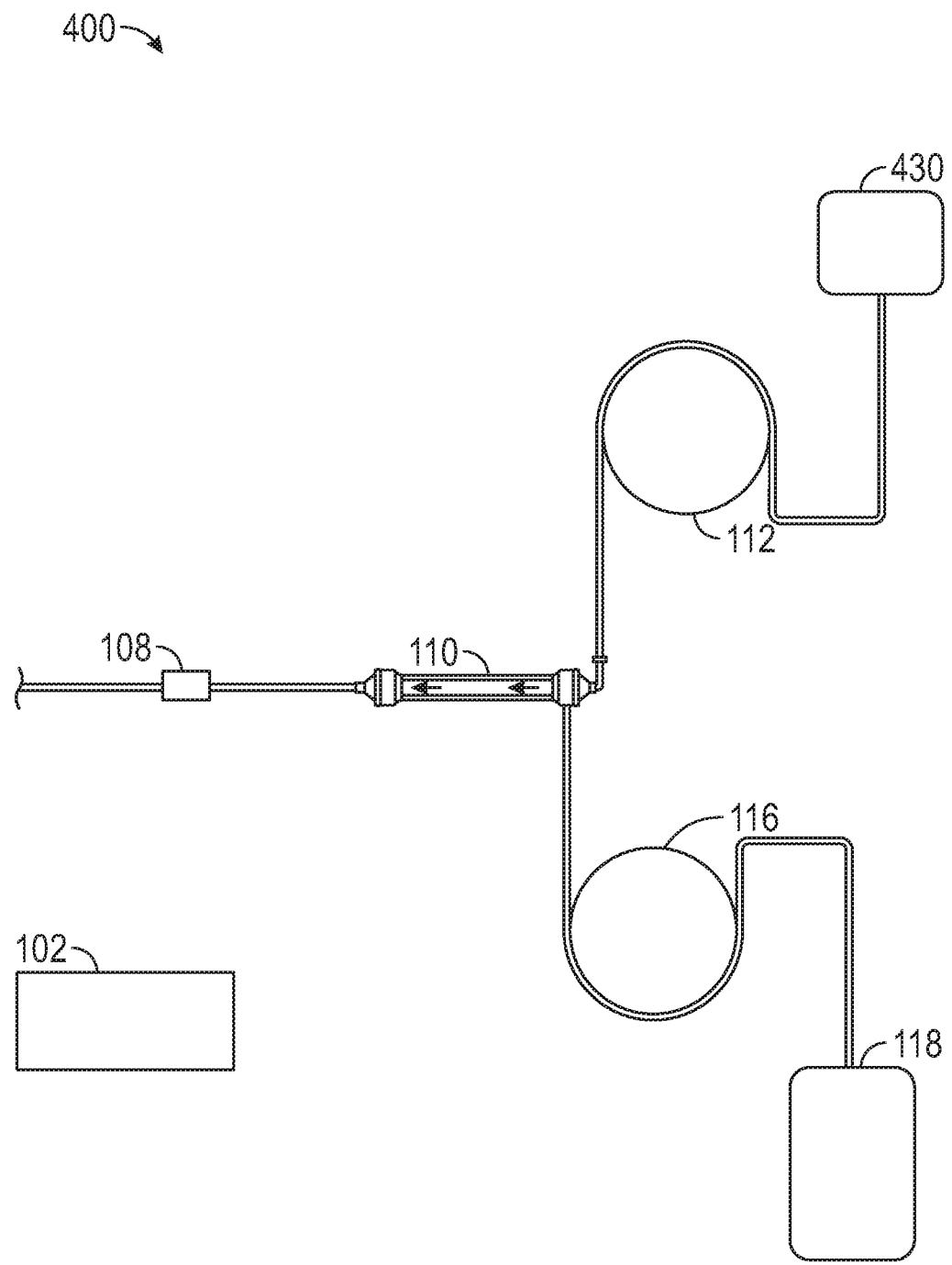

FIG. 4D shows another example of the blood filtration system 400. In some examples, the blood filtration system 400 does not include the one or more check valves 122. For instance, the blood pump 112 can withdraw blood from the catheter and transmit the blood into the blood reservoir 430. The operating direction of the blood pump 112 can be changed (e.g., operated in the second flow direction) to transmit blood back into the filter 110. For instance, the blood in the system 400 can be transmitted through the filter 110 in a plurality of cycles. In another example, for instance as shown in FIG. 4A, blood can be transmitted through the filter 110 in a single cycle (e.g., in a continuous circuit). The controller 102 can be configured to operate the filtration pump 116 during a single cycle through the filter 110, or to operate the filtration pump 116 during one or more of the plurality of cycles through the filter 110.

Figure 4E:
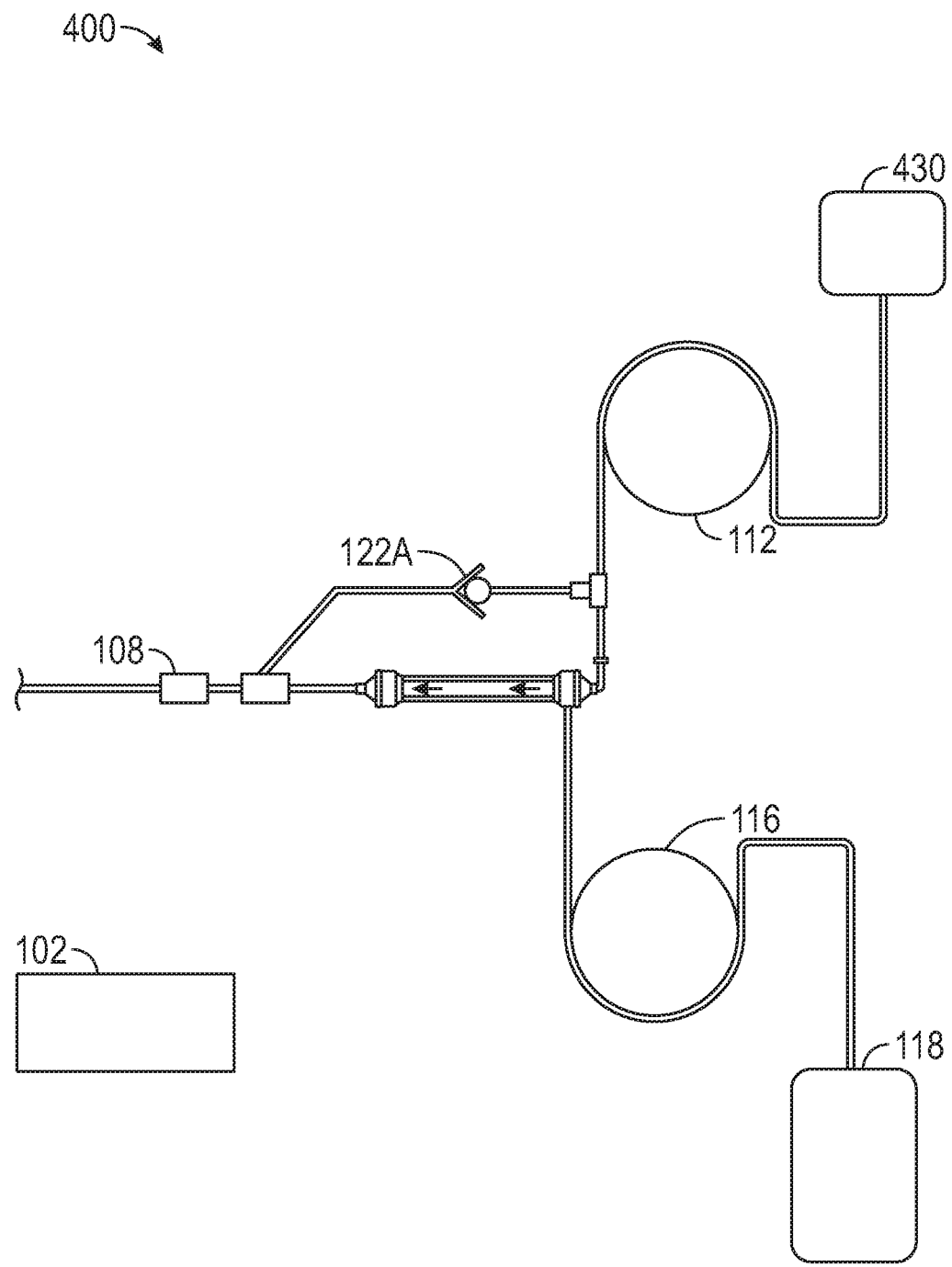
Figure 4F:
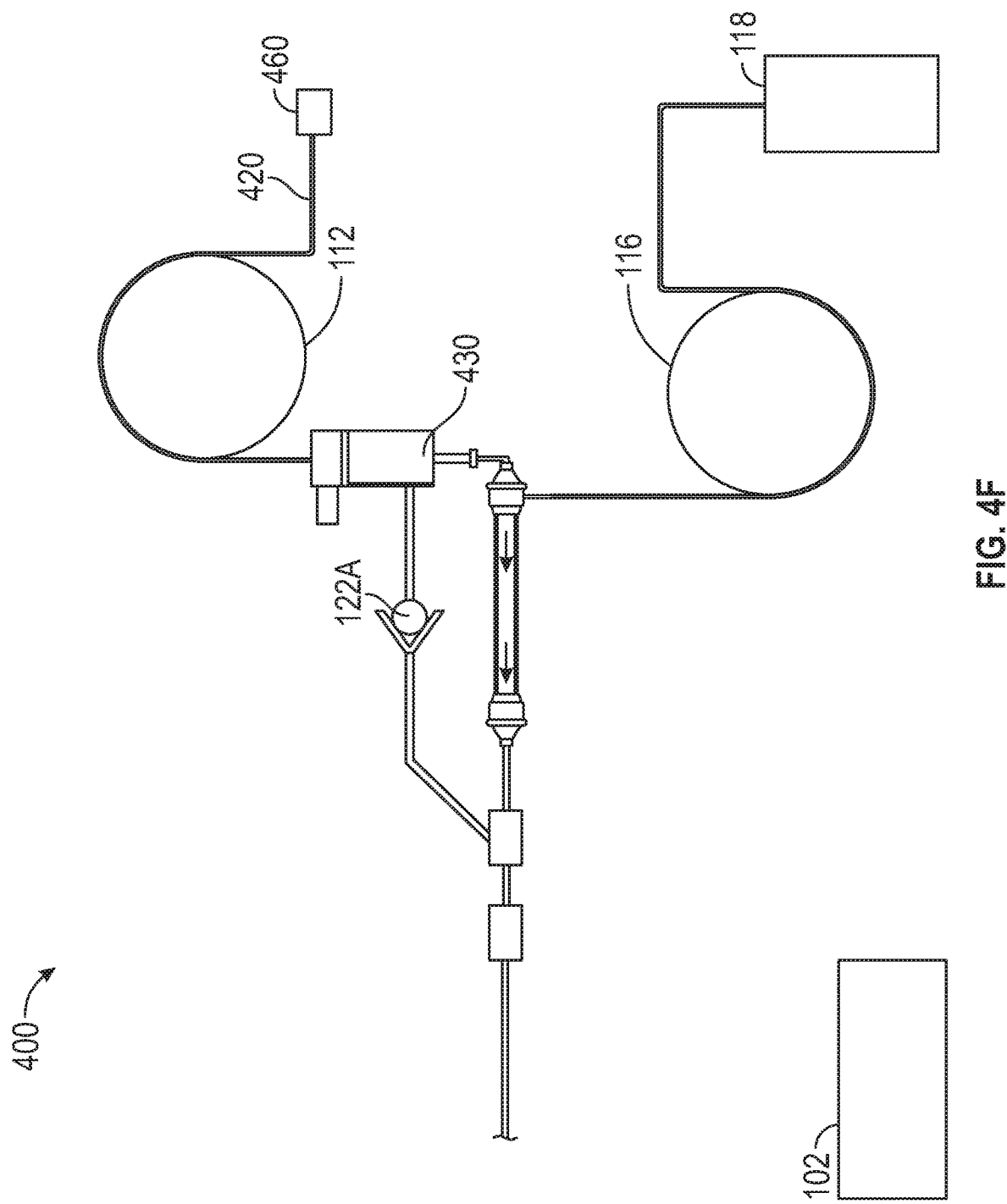
Figure 4G:
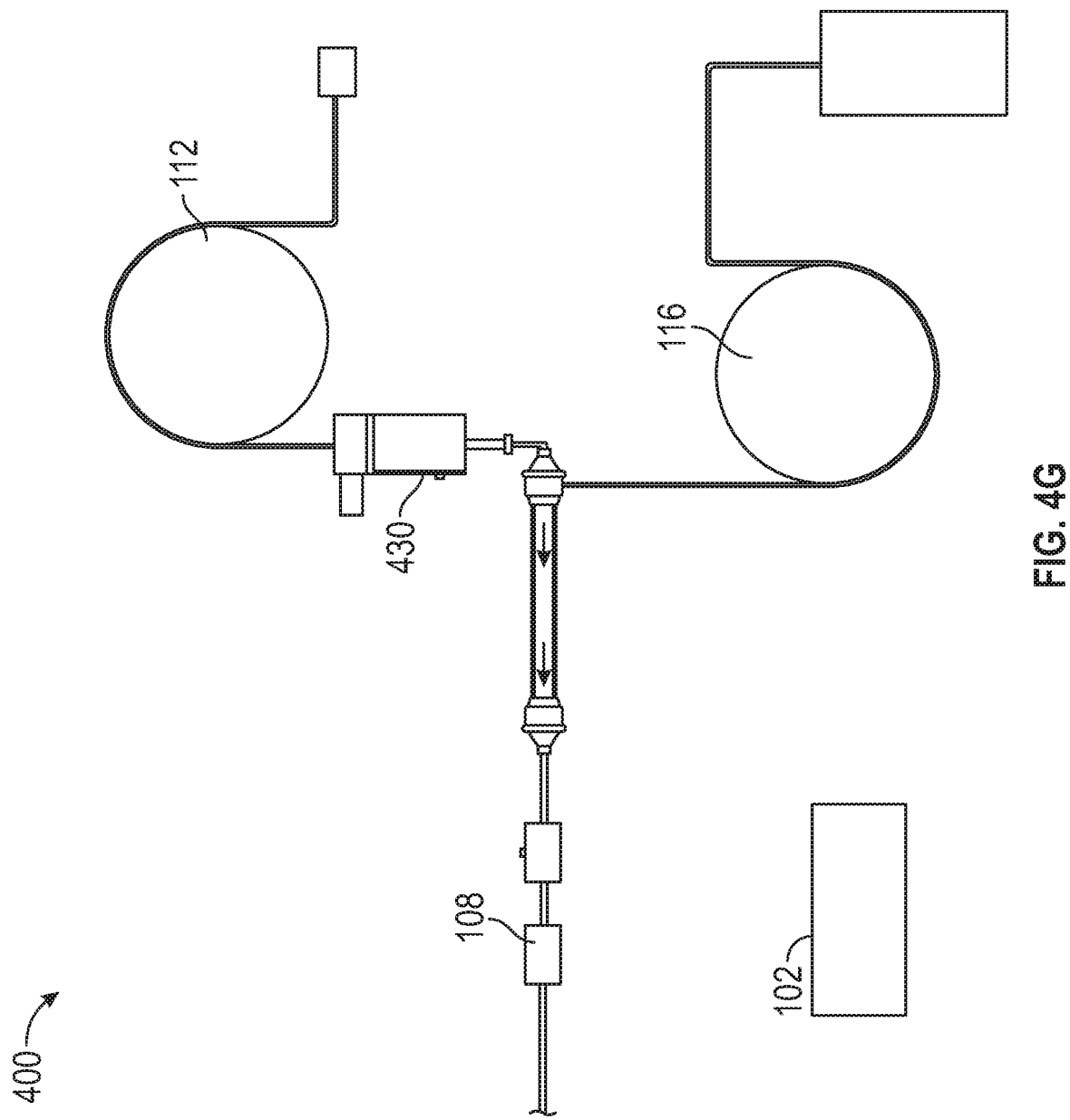
Figure 4H:
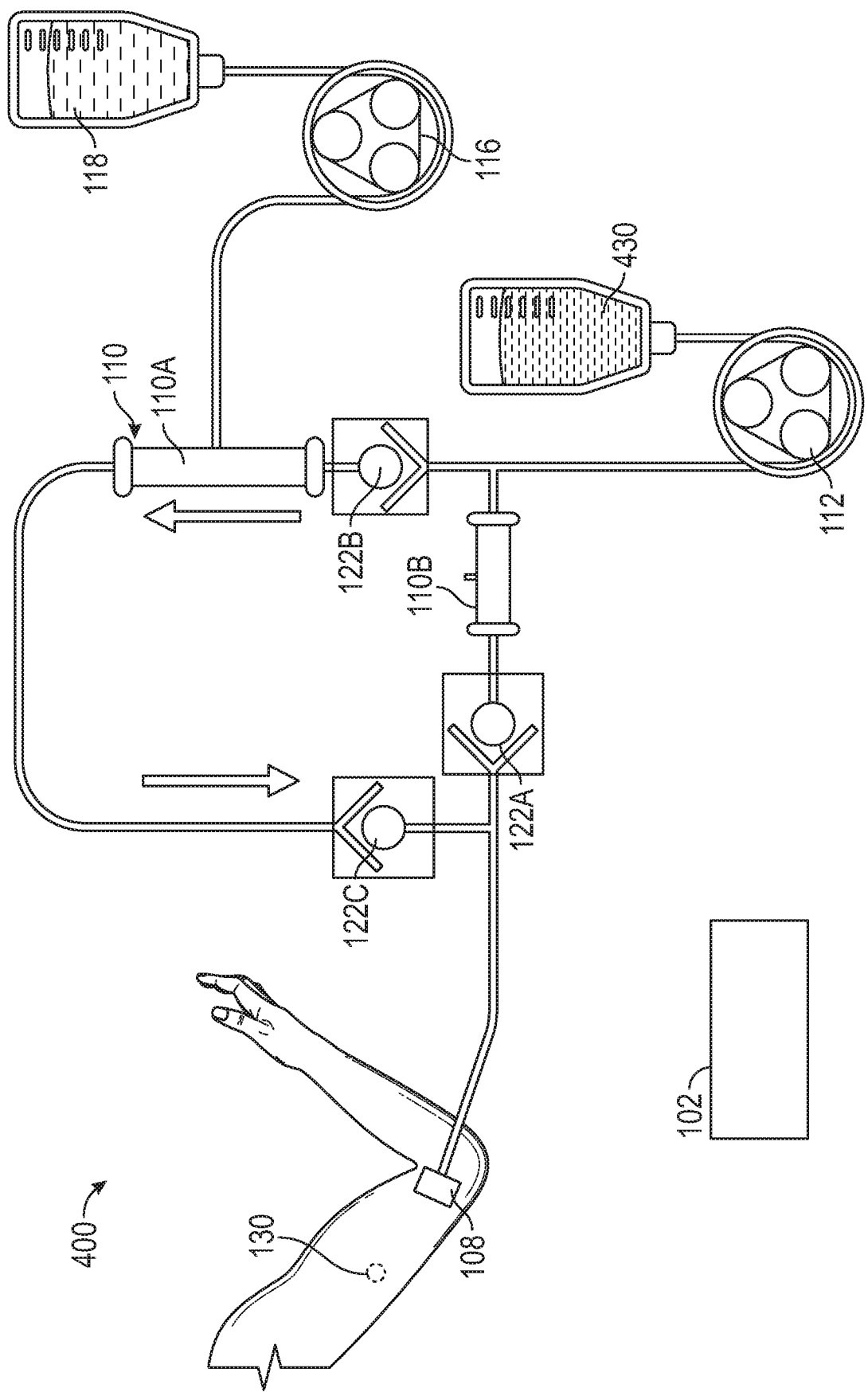

As shown in FIG. 4E, the blood filtration system 400 can include a single valve 122. Blood can be transmitted from the catheter 108, through the valve 122A, and into the blood reservoir 430. The operating direction of the blood pump 112 can be reversed, and blood can be transmitted through the filter 110 and into the catheter 108. In some examples, and as shown in FIGS. 4F-4G, the blood pump 112 can pump a gas (e.g., air, nitrogen, or the like) to correspondingly pump blood into and out of the blood reservoir 430. For instance, the blood pump 112 can decrease the gas pressure in the blood reservoir 430, and correspondingly draw blood into the blood reservoir from the catheter 108. The operating direction of the blood pump 112 can be changed, and the gas pressure inside the blood reservoir 430 can be increased. In this example, the increase in gas pressure can correspondingly cause the blood flow from the blood reservoir 430 and into the filter 110. In some examples the blood filtration line 420 can be in communication with the atmosphere, for instance through an air filter 460. The communication of the blood filtration line 420 with the atmosphere can facilitate the blood pump 112 changing the pressure within the blood reservoir 430.

Further, and as described in greater detail herein, the blood filtration system 400 can include one or more filters 110. For example, the blood filtration system 400 can include a first filter 110A and a second filter 110B. In this example, the filters 110A, 100B are in communication with the filtration pump 116 (or a plurality of filtration pumps 116), and the filtration pump 116 extracts filtrate fluid from the filters 110A, 110B. In an example, the filter 110A filters filtrate fluid from the blood of the patient when the blood pump 112 operates in a first direction (e.g., during withdrawal of blood from the patient). In another example, the filter 110B filters filtrate fluid from the blood of the patient when the blood pump operates in a second direction (e.g., during infusion of blood into the patient). The system 100 can determine the amount of filtrate fluid removed from the blood of a patient. For example the system 100 can be in communication with a scale that weights the reservoir 118. In another example, the sensors 124 can include a flow meter in communication with the line 114 and the controller 102 determines the amount of filtrate fluid removed from the patient with the flow meter.

Figure 5:
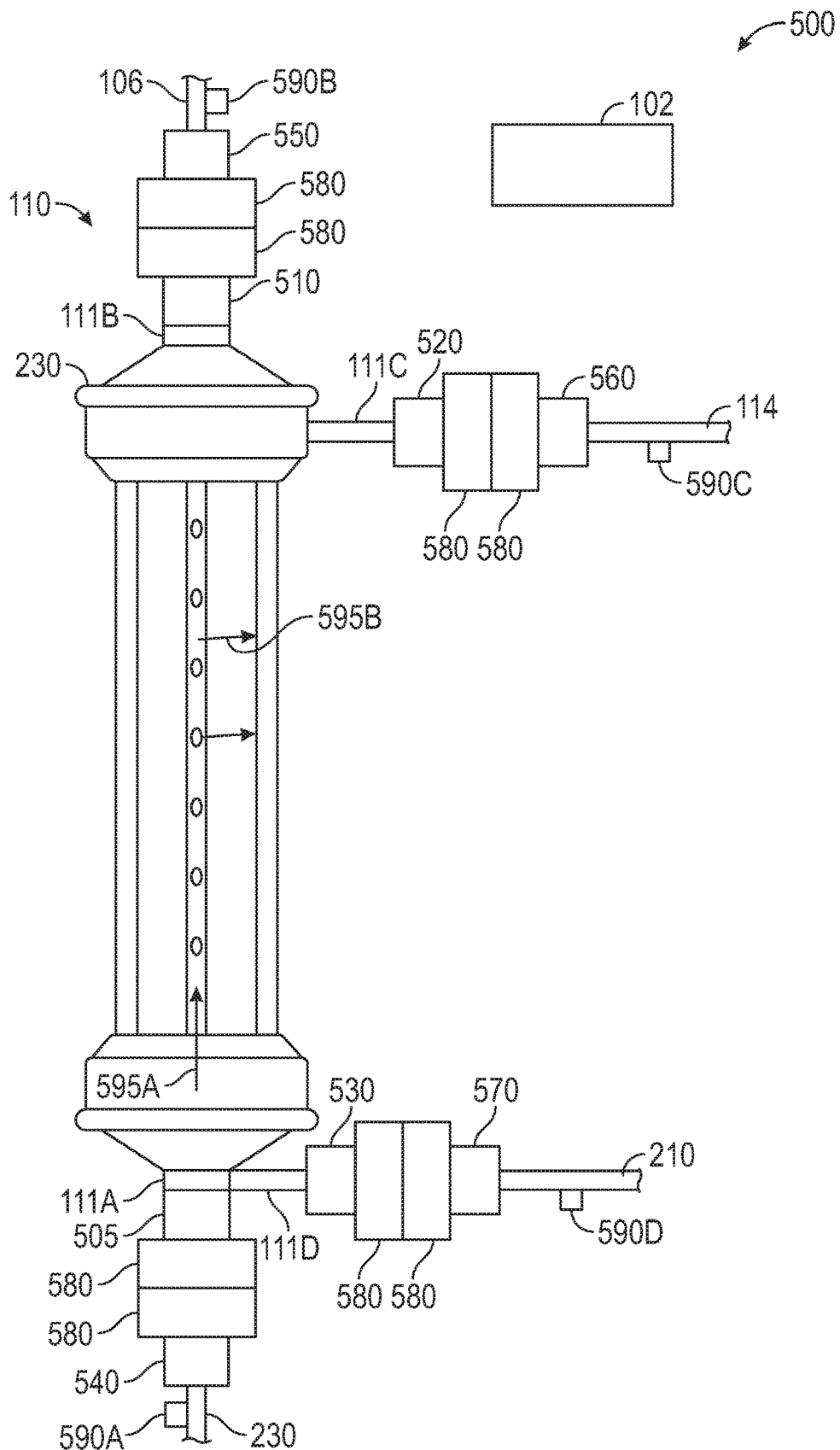
FIG. 5 shows a schematic view of a fourth blood filtration system.

FIG. 5 shows a schematic view of a fourth blood filtration system 500. As described herein, the filter 110 can include a filter body 230, a filter inlet port 111A, a filter outlet port 111B, and a filtrate fluid port 111C. The filter inlet port 111A, filter outlet port 111B, and filtrate fluid port 111C can be included in the filter body 230, and the ports 111A, 111B, 111C facilitate coupling the filter 110 with additional components of a blood filtration system (e.g., one or more of the blood filtration systems 100, 200, 400).

In an example, blood can flow into the filter body 230 through the filter inlet port 111A, flow through the filter body 230, and out of the filter outlet port 111B. In an example, blood can cycle through the filter 110 multiple times, for instance as described with reference to FIG. 4G. The filter 110 can be configured to reduce the amount of filtrate fluid in the blood flowing through the filter 110, and transmit the extracted filtrate fluid to the filtrate fluid port 111C.

As described herein, the filter 110 can include the harvesting port 111D. In some examples, the harvesting port 111D can be coupled to the filter inlet port 111A, and the harvesting port 111D can be in communication with the filter inlet port 111A. Introducing filtrate fluid into the harvesting port 111D can mix filtrate fluid with blood entering the filter inlet port 111A, and accordingly dilute the blood with the filtrate fluid.

In some examples, the filter 110 can include one or more valves to inhibit the flow of fluid with respect to the filter 110. In an example, the filter can include a filter inlet valve 505, a filter outlet valve 510, a filtration fluid valve 520, and/or a harvesting valve 530. The valves 505, 510 can be in communication with the ports 111A, 111B, respectively, and can stop (e.g., inhibit) the flow of blood with respect to the filter 110 (e.g., preventing the transmission of blood into or out of the ports 111A, 111B). The valve 520 can be in communication with the port 111C, and can stop the flow of filtrate fluid with respect to the filter 110 (e.g., preventing the transmission of blood into or out of the port 111C). The valve 530 can be in communication with the port 111D, and can stop the flow of filtrate fluid and/or blood with respect to the filter 110 (e.g., preventing the transmission of filtrate fluid and/or blood into or out of the port 111D).

Additionally, the withdrawal line 104 can be in communication with a first line valve 540, the infusion line 106 can be in communication with a second line valve 550, the filtrate fluid line 114 can be in communication with a third line valve 560, and the harvesting line 210 can be in communication with a fourth line valve 570. The valves 540, 550, 560, 570 can stop the flow with respect to the lines 104, 106, 114, 210, respectively.

The valves 505, 510, 520, 530, 540, 550, 560, 570 can facilitate interchanging the filter 110 with a different filter 110, for instance if the filter 110 becomes clogged. For instance, the valves 505, 510, 520, 530, 540, 550, 560, 570 can be closed, and coupling members 580 (e.g., fittings) can be separated to detach the lines 104, 106, 114, 210 from the filter. A replacement filter 110 can be located proximate to the lines 104, 106, 114, 210, and the coupling members 180 can be reattached to the replacement filter 110. The valves 505, 510, 520, 530, 540, 550, 560, 570 can be opened, and flow throughout the blood filtration system 500 is reestablished. Accordingly, the performance of the blood filtration system 500 is thereby improved. In some examples, the members 580 are integral with the valves 505, 510, 520, 530, 540, 550, 560, 570.

In an example, the valves 540, 550, 560, 570 include a ball valve. In another example, the valves 540, 550, 560, 570 include one or more pinch valves that compresses the lines 104, 106, 114, 210 to inhibit the flow of fluid through one or more of the lines 104, 106, 114, 210. In an example, the controller 102 operates the pinch valves to inhibit flow of fluid through the lines 104, 106, 114, and 210.

The blood filtration system 500 can include the controller 102, and the controller 102 can be configured to determine one or more filter resistances of the filter 110. In an example, the filter 110 can have a longitudinal resistance characteristic, and the longitudinal resistance characteristic can include the resistance of the flow of a fluid (e.g., blood) through a length of the filter 110, for instance as denoted by the arrow 595A. In one example, the controller 102 can determine the longitudinal filter resistance characteristic by determining the pressure at an inlet pressure sensor 590A that is in communication with the inlet port 111A of the filter 110.

As the filter 110 filters blood, the filter 110 can become clogged, for instance due to clotting in the filter 110. As the filter 110 becomes clogged, the longitudinal filter resistance of the filter 110 increases, because the clogged filter increases the amount of force necessary to pump blood through the filter 110. Accordingly, the pressure at the inlet pressure sensor 590A can increase.

The controller 102 can compare longitudinal filter resistance characteristic to a filter resistance threshold, for instance a first filter resistance threshold, and determine if the longitudinal filter resistance characteristic exceeds the first filter resistance threshold. In this example, when the longitudinal filter resistance exceeds (e.g., is greater than) the first filter resistance threshold, the controller 102 can operate (e.g., with a control signal) a harvesting pump (e.g., the harvesting pump 220 shown in FIG. 1). Operating the harvesting pump can inject a fluid (e.g., filtrate fluid, saline, heparin, or the like) into the port 111D, and introduce the fluid into blood flowing into the filter 110. For instance, injecting the filtrate fluid into the port 111D can reduce the longitudinal filter resistance characteristic, for instance by diluting blood clotted in the filter 110. The controller 102 can be configured to operate the harvesting pump and stop injecting filtrate fluid into the port 111D when the longitudinal filter resistance characteristic exceeds (e.g., is less than) a second filter resistance threshold. Accordingly, the performance of the blood filtration system 500 is improved because a lifetime of the filter 110 can be extended by reducing clogging of the filter 110.

In another example, the filter 110 can have a transverse resistance characteristic, and the transverse resistance characteristic can include the resistance of the flow of a fluid (e.g., filtrate fluid) through a thickness of the filter 110, for instance as denoted by the arrow 595B. In one example, the controller 102 can determine the transverse filter resistance characteristic by determining the pressure at a filtration pressure sensor 590C that is in communication with the filtrate fluid port 111C of the filter 110. As the filter 110 filters blood, the filter 110 can become clogged, for instance due to clotting in the filter 110. As the filter 110 becomes clogged, the transverse filter resistance of the filter 110 increases, because the clogged filter increases the amount of force necessary to extract filtrate fluid from the filter 110 (e.g., with the filtration pump 116 shown in FIG. 1). Accordingly, the pressure at the inlet pressure sensor 590A can increase.

The controller 102 can compare the transverse resistance characteristic to a filter resistance threshold, for instance a first filter resistance threshold, and determine if the transverse resistance characteristic exceeds (e.g., is greater than) the first filter resistance threshold. In this example, when the transverse filter resistance exceeds the first filter resistance threshold, the controller 102 can operate (e.g., with a control signal) a harvesting pump (e.g., the harvesting pump 220 shown in FIG. 1). Operating the harvesting pump can inject filtrate fluid into the port 111D, and dilute the blood flowing into the filter 110. Injecting the filtrate fluid into the port 111D can reduce the transverse filter resistance characteristic, for instance by diluting blood clotted in the filter 110. The controller 102 can be configured to operate the harvesting pump and stop injecting filtrate fluid into the port 111D when the transverse filter resistance characteristic exceeds (e.g., is less than) a second filter resistance threshold. Accordingly, the performance of the blood filtration system 500 is improved because a lifetime of the filter 110 can be extended by reducing clogging of the filter 110.

Figure 6:
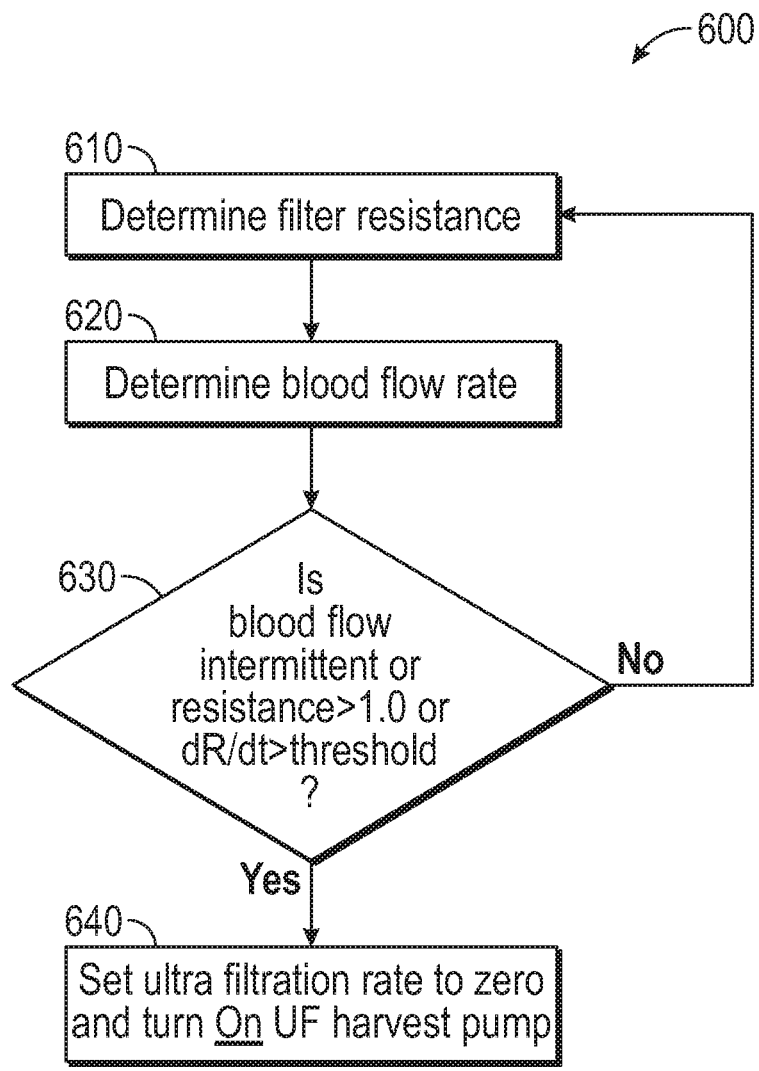
FIG. 6 shows a flowchart for a second method for preserving a filter for a blood filtration system.

FIG. 6 shows a flowchart for a second method 600 for preserving a filter for a blood filtration system. In describing the method 600, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 600 include, but are not limited to, the corresponding numbered elements provided herein and other corresponding elements described herein (both numbered and unnumbered) as well as their equivalents. Additionally, the method 600 can be included in instructions on a computer readable medium, and the instructions can be carried out by the controller 102 (e.g., processing circuitry).

At operation 610, a filter resistance can be determined. In some examples, the controller 102 compares pressure at the inlet pressure sensor 590A or the filtration pressure sensor 590C to an outlet pressure sensor 590B or a harvesting pressure sensor 590D to determine the filter resistances, or to improve the accuracy of the filter resistance determinations. In an example, the transverse filter resistance can be calculated according to the pressure differential between the outlet pressure sensor 590B and the filtration pressure sensor 590C, and dividing the pressure differential by the flow rate of the filtration pump (e.g., the filtration pump 116 shown in FIG. 1). In another example, the longitudinal filter resistance can be calculated according to the pressure differential between the inlet pressure sensor 590A and the filtration pressure sensor 590C, and dividing the pressure differential by the flow rate of the blood pump (e.g., the blood pump 112 shown in FIG. 1).

At operation 620, the blood flow rate can be determined, for instance by determining the operating rate of the blood pump 112, shown in FIG. 1. At operation 630, the controller 102 can determine if the blood flow rate is intermittent (e.g., varying, fluctuating, or the like) and accordingly the controller 102 can operate the filtration pump 116 (e.g., stop the filtration pump) and operate the harvesting pump 220 (e.g., operate the harvesting pump 220 to inject filtrate fluid into the harvesting port 111D). Additionally, the controller can determine if one or more filter resistances are greater than a filter resistance threshold and accordingly the controller 102 can operate the filtration pump 116 and operate the harvesting pump 220. Additionally, the controller 102 can monitor the blood flow rate over time (e.g., by determining the blood flow rate with the one or more sensors 124), and when the blood flow rate decreases over time below a blood flow rate threshold, the controller 102 can operate the filtration pump 116 and operate the harvesting pump 220. Accordingly, the method 600 can reduce clogging in the filter and improve the performance of a blood filtration system.

Figure 7:
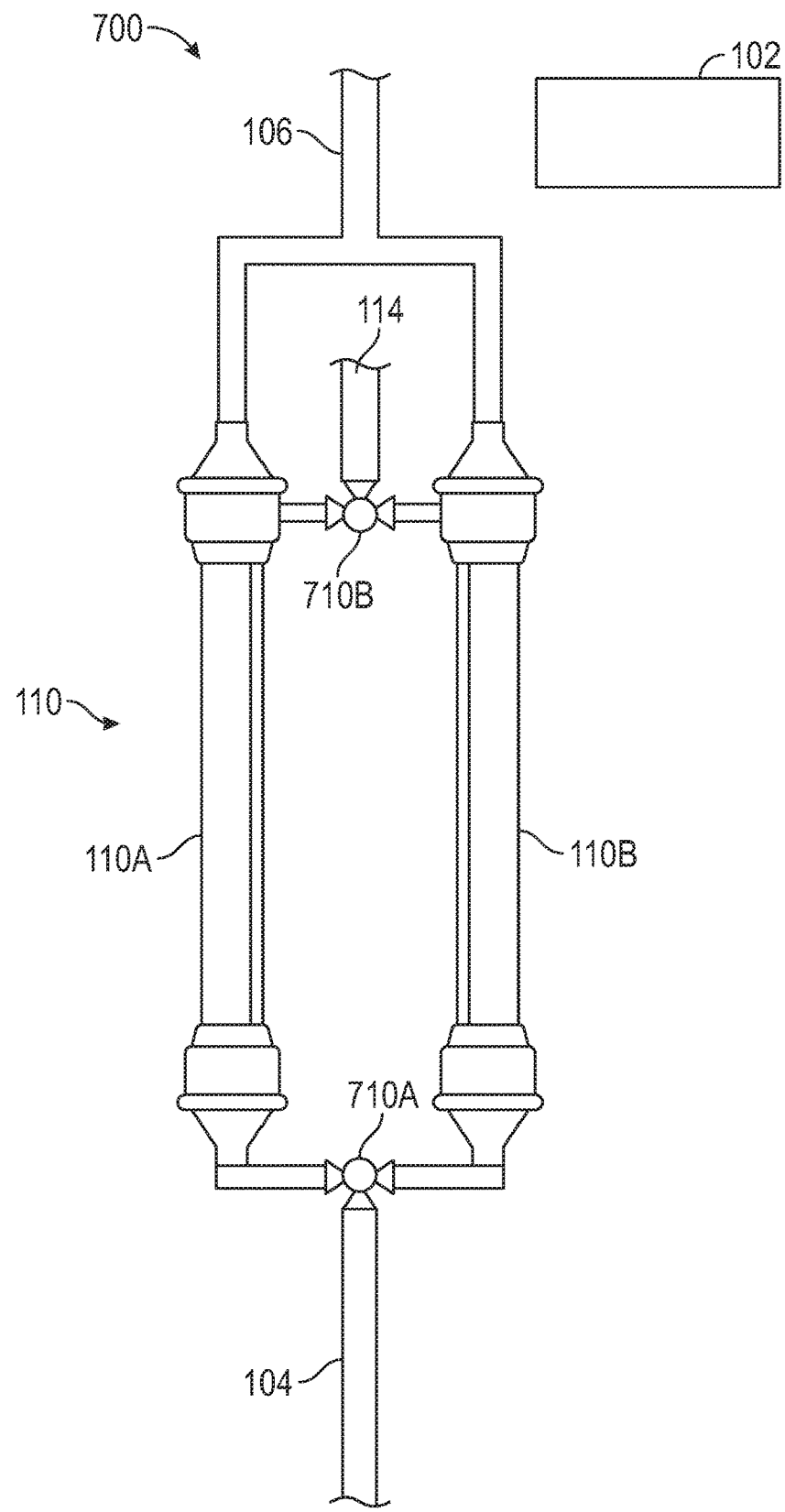
FIG. 7 shows a schematic view of a fifth blood filtration system.

FIG. 7 shows a schematic view of a fifth blood filtration system 700. The blood filtration system can include on or more filters 110, for instance a first filter 110A or a second filter 110B. In an example, and as shown in FIG. 7, the filters 110A, 110B can be arranged in parallel. In another example, the filters 110A, 110B can be arranged in series. The blood filtration system can include a first valve 710A and can include a second valve 710B. The valves 710A, 710B can facilitate the flow of fluids (e.g., blood or filtrate fluid) through the system 500.

In an example, the valve 710A can be configured to divert blood flow through the filter 110A or the filter 110B. For instance, the valve 710A can be operated (e.g., by a user, or the controller 102, for example with a control signal) to divert the flow of blood between the filters 110A, 110B. In another example, the valve 710B can be operated (e.g., by a user, or the controller 102, for example with a control signal) to divert the facilitate the extraction of filtrate fluid from the filters 110A, 110B.

Figure 8A:
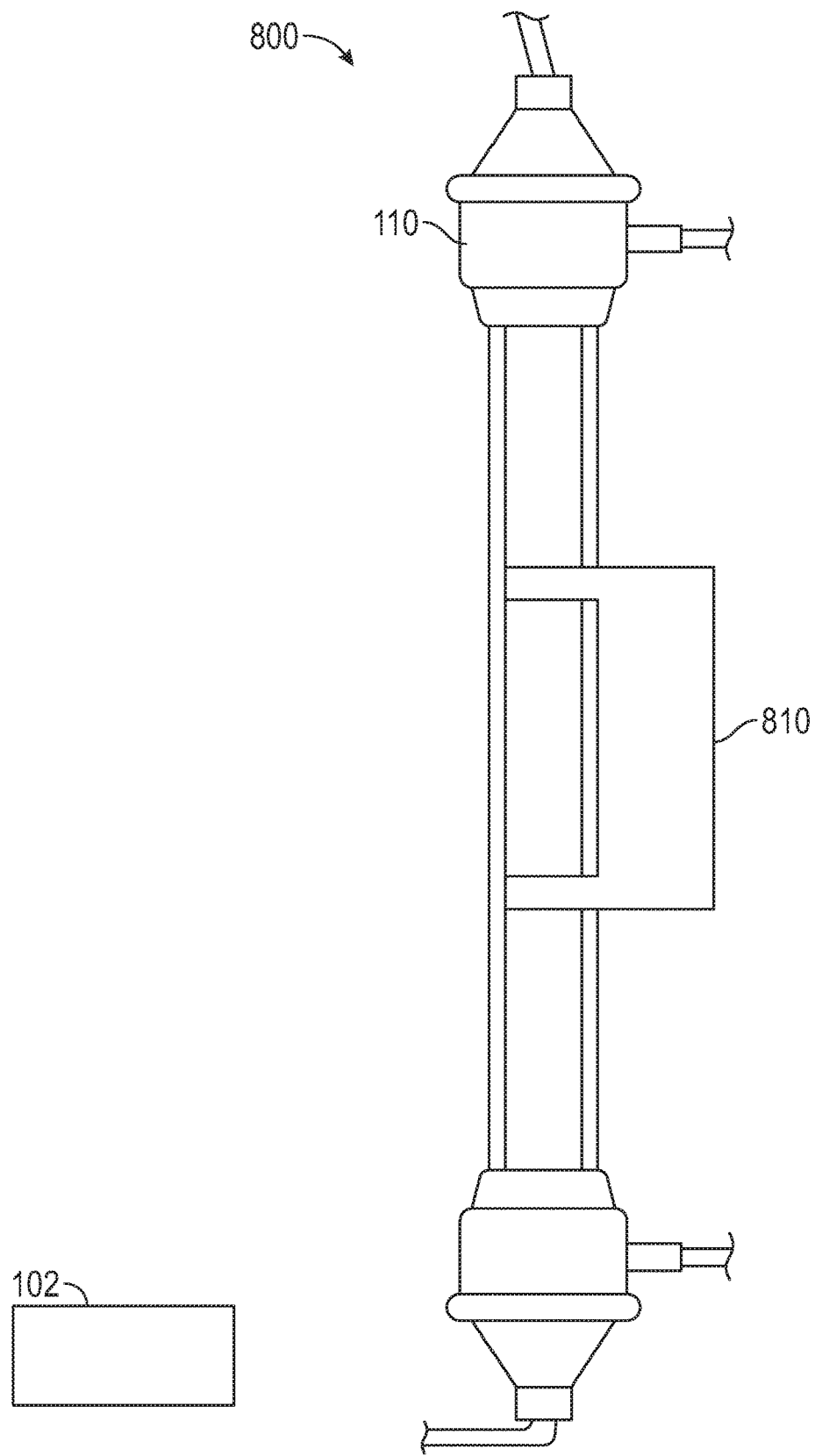
FIGS. 8A-8B shows a schematic view of a sixth blood filtration system.

FIG. 8A shows a schematic view of a sixth blood filtration system 800. The blood filtration system 800 can include an agitator 810 coupled with the filter 110. In an example, the agitator 810 can provide vibrations to the filter 110. In an example, the agitator 810 can include a piezoelectric element, and the agitator 810 can be operated by the controller 102 (e.g., with a control signal, for instance a control signal in communication with a relay that energizes the piezoelectric element). In another example, the agitator 810 can include an ultrasound generator that in some examples is operated by the controller 102.

The agitator 810 can reduce clogging in the filter 110, for instance when blood clots in the filter 110. In an example, the controller 102 can operate the agitator 810 when a filter resistance (e.g., the longitudinal filter resistance) exceeds a filter resistance threshold (e.g., the first filter resistance threshold), Accordingly, the agitator 810 can improve the performance of the blood filtration system 800, for instance by providing a vibration to the filter 110 and thereby reducing clotting of blood within the filter 110.

Figure 8B:
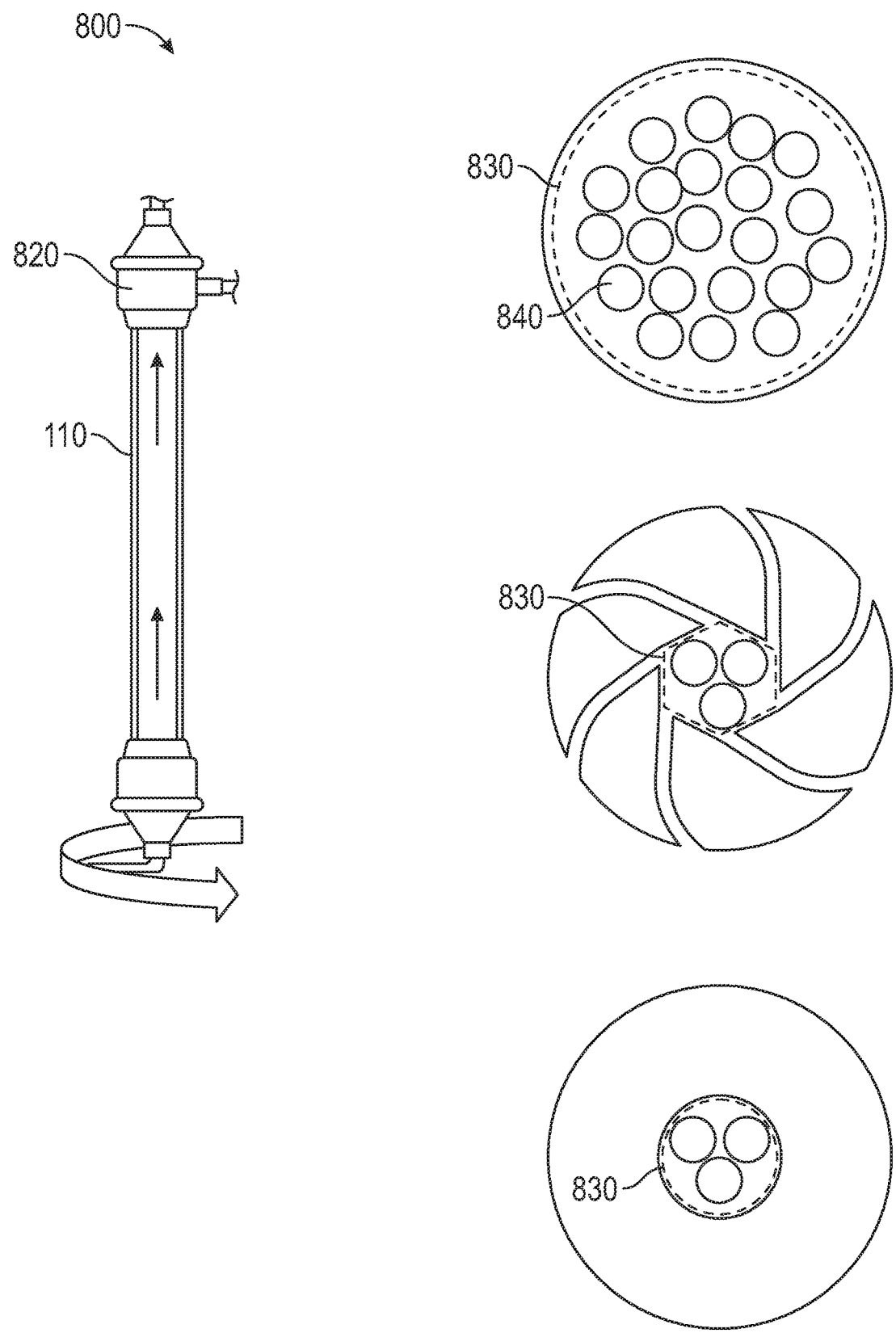

As shown in FIG. 8B, the filter 110 can have a variable volume. In an example, a filter cap 820 can be operated (e.g., rotated, turned, twisted, engaged with, or the like) and the volume of the filter 110 can correspondingly vary. For instance, operation of the filter cap can change the dimension of an aperture 830 (e.g., by changing a dimension of an iris mechanism, a Tuohy Borst mechanism, or the like). Changing the dimension of the aperture 830 can block one or more portions of the filter, for instance filter fibers 840, and change the volume of the filter 110. In some examples, the volume of the filter 110 is adjusted to meet patient needs. For instance, a child can have its blood filtered by the blood filtration system 800, and the volume of the filter 110 can be adjusted to accommodate for the reduced stature of the child. The variable volume of the filter 110 allows for a filter to have a variable filtration capacity (e.g., the amount of filtrate fluid that is extracted by the filter 110), and accordingly improves the performance of the blood filtration system 800.

Figure 9:
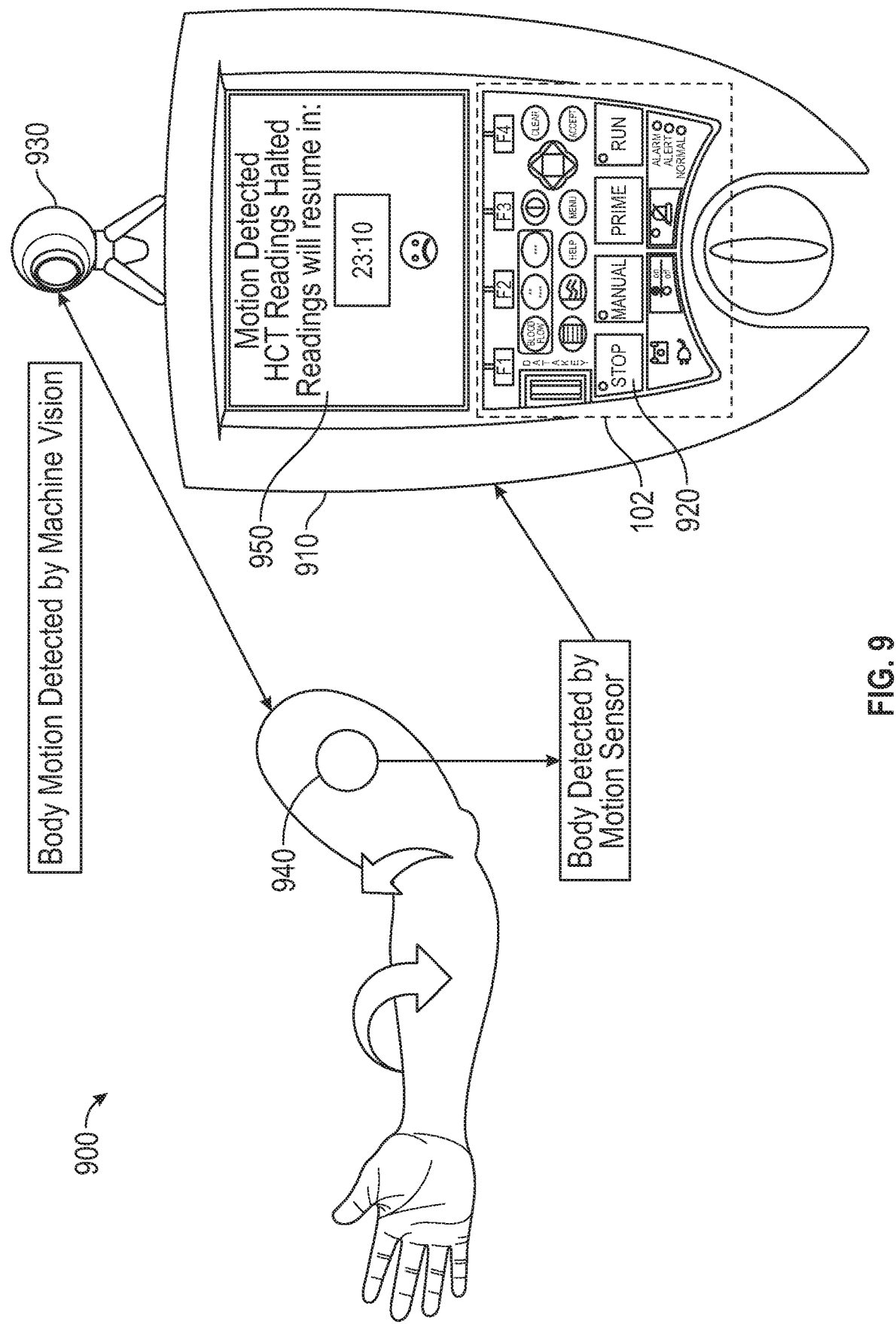
FIG. 9 shows a schematic view of a seventh blood filtration system.

FIG. 9 shows a schematic view of a seventh blood filtration system 900. The blood filtration system 900 can include a system housing 910 that includes controls 920 (e.g., buttons) that can change various operating parameters of the system 900, for instance a button that operates the blood pump 112 (shown in FIG. 1). The system housing 910 can include the controller 102, and the controls 920 can communicate with the controller 102 to operate one or more components of the blood filtration system (e.g., the harvesting pump 220 shown in FIG. 2).

The blood filtration system 900 can include an optical sensor 930 (e.g., a camera, an infrared camera, or the like) that can monitor movement of the patient, for instance my observing a patient reference point 940 (e.g., a head of the patient, a mark included on a surface of an object secured to the patient, for instance a blood pressure cuff, or the like). The optical sensor 930 can monitor the position of the patient reference point and the controller 102 can be configured to determine if movement of the patient from an initial position affects the determined hematocrit value of the patient. The hematocrit value determination can be affected by movement of a patient, for example when the patient transitions from a supine position (e.g., laying down) to a standing position.

In an example, the controller 102 can be configured to provide a notification if the hematocrit determination is affected by the movement of the patient. For instance, the controller 102 can provide a notification on a display 950 with a timer indicating the time since the patient moved in a way that affected the hematocrit value determination. In an example, the controller 102 can compare the change in position of the portion of the body of the patient to a positional threshold and provide a notification when the change in position exceeds the positional threshold. For instance, the controller 102 can determine the position of the patient reference point 940 relative to the optical sensor 930.

In yet another example, the controller 102 can operate a speaker and change a tone according to the patient movement (e.g., initiate a beep if the patient moves). Additionally, the controller 102 can determine a movement value for instance a difference between the position of the patient reference point to the initial position. Further, the controller can compare the movement value to a movement threshold and can provide a notification if the movement value exceeds the movement threshold.

In another example, the controller 102 can refrain from providing a notification of the hematocrit value when the hematocrit value is affected by movement of the patient (e.g., by refraining from displaying the movement-affected hematocrit value on the display 950). Accordingly, the blood filtration system 900 can provide additional information (e.g., to a healthcare provider) that the hematocrit value of the patient has been affected by movement of the patient.

In yet another example, the patient reference point 940 can include an accelerometer, and the accelerometer can be in communication with the controller 102 (e.g., with a wired or wireless communication pathway). The accelerometer can monitor the movement of the patient by determining acceleration of a portion of a body of the patient (e.g., an arm). The controller 102 can determine if the movement of the patient from the initial position affects the determined hematocrit value of the patient, for instance by comparing the acceleration of the portion of the body of the patient to an acceleration threshold.

In still yet another example, a pressure sensor in communication with a blood stream of the patient (e.g., the first sensor 124A or the second sensor 124B shown in FIG. 1) can monitor a change in pressure within the blood stream of the patient. The controller 102 can determine if the movement of the patient from the initial position affects the determined hematocrit value of the patient, for instance by comparing the change in pressure (e.g., because the patient transitioned from laying down to standing) within the blood stream to a pressure threshold. The controller 102 can provide a notification if the change in pressure exceeds the pressure threshold.

In some examples, the controller 102 can apply a correction value to the determined hematocrit value of the patient according to the movement of the patient. For instance, the correction value can be determined by evaluating a change in the hematocrit value according to the motion of the patient. The controller 102 can log data associated with changes in patient position and corresponding changes in hematocrit values to determine the correction value.

Figure 10:
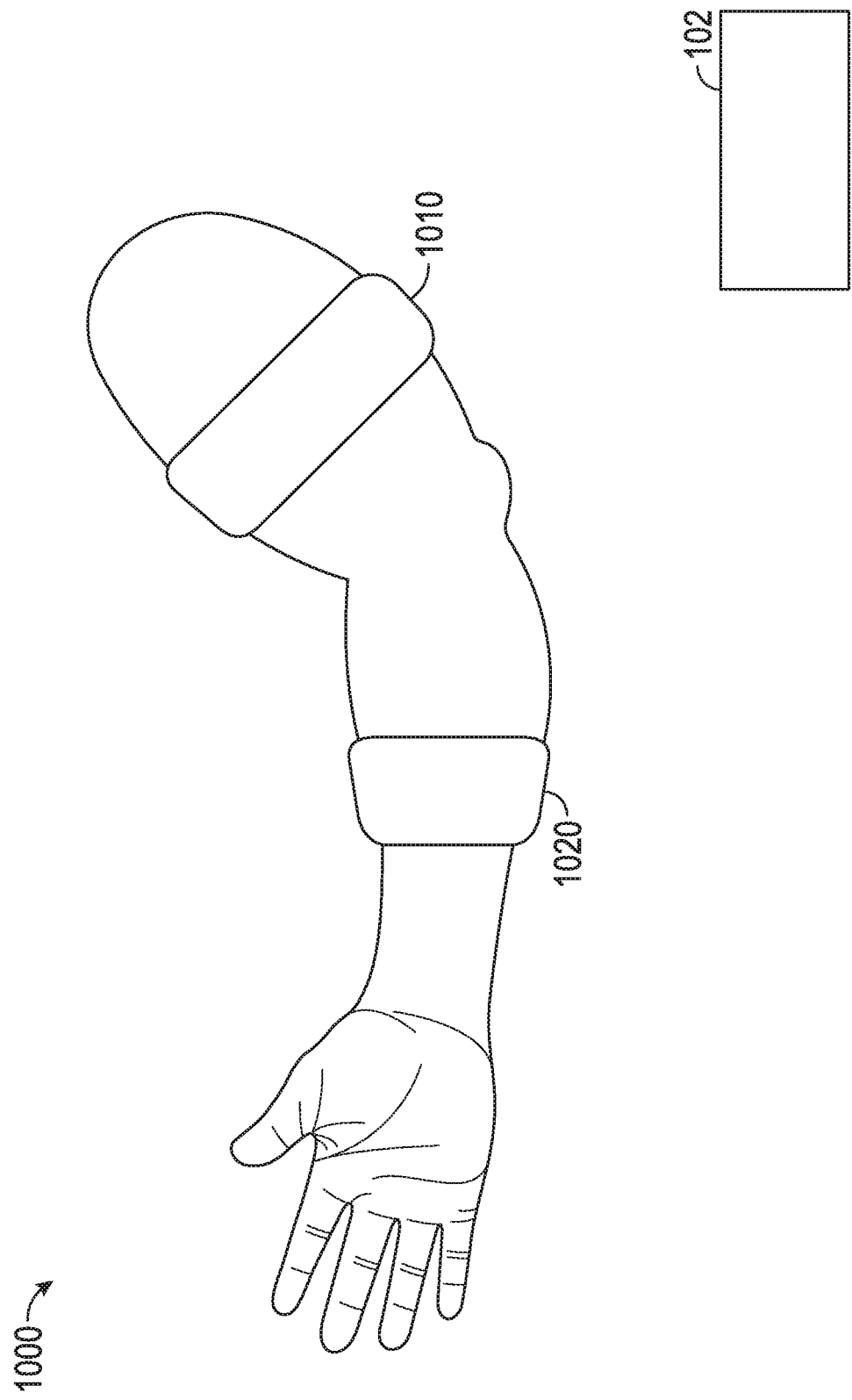
FIG. 10 shows a schematic view of an eighth blood filtration system.

FIG. 10 shows a schematic view of an eighth blood filtration system 1000. The blood filtration system 1000 can include a proximal venous occlusion cuff 1010 and can include a distal venous occlusion cuff 1020. The cuffs 1010, 1020 can engage with an arm of the patient to encourage blood flow in the arm of the patient. In an example, the controller 102 can operate the cuffs 1010, 1020 to constrict the cuff 1010 or the cuff 1020. Constricting the cuffs 1010, 1020 can cause the blood pressure in the arm to increase. The controller 102 can operate the cuff 1010 to loosen the cuff 1010, or the 1020, which can encourage blood flow in the arm, for instance by increasing blood flow into the catheter 108 (shown in FIG. 1).

The controller 102 can operate the cuffs 1010, 1020 to synchronize the cuffs 1010, 1020. In an example, the controller 102 can operate the cuffs 1010, 1020 to tighten the cuffs 1010, 1020 at the same point in time. In another example, the controller 102 can operate the cuffs 1010, 1020 to loosen the cuffs 1010, 1020 at the same point in time. In yet another example, the controller 102 can operate the cuffs 1010, 1020 to tighten the cuff 1010, while the cuff 1020 is loosened. In still yet another example, the controller 102 can operate the cuffs 1010, 1020 to tighten the cuff 1020, while the cuff 1010 is loosened.

Figure 11A:
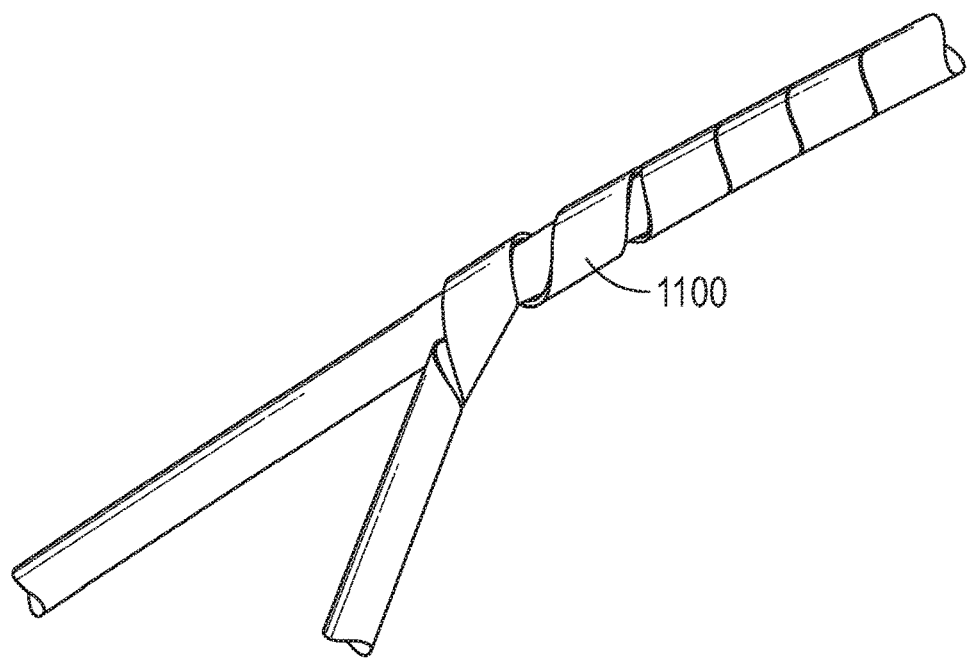
FIGS. 11A-11B are photographs of line protectors for a blood filtration system.
Figure 11B:
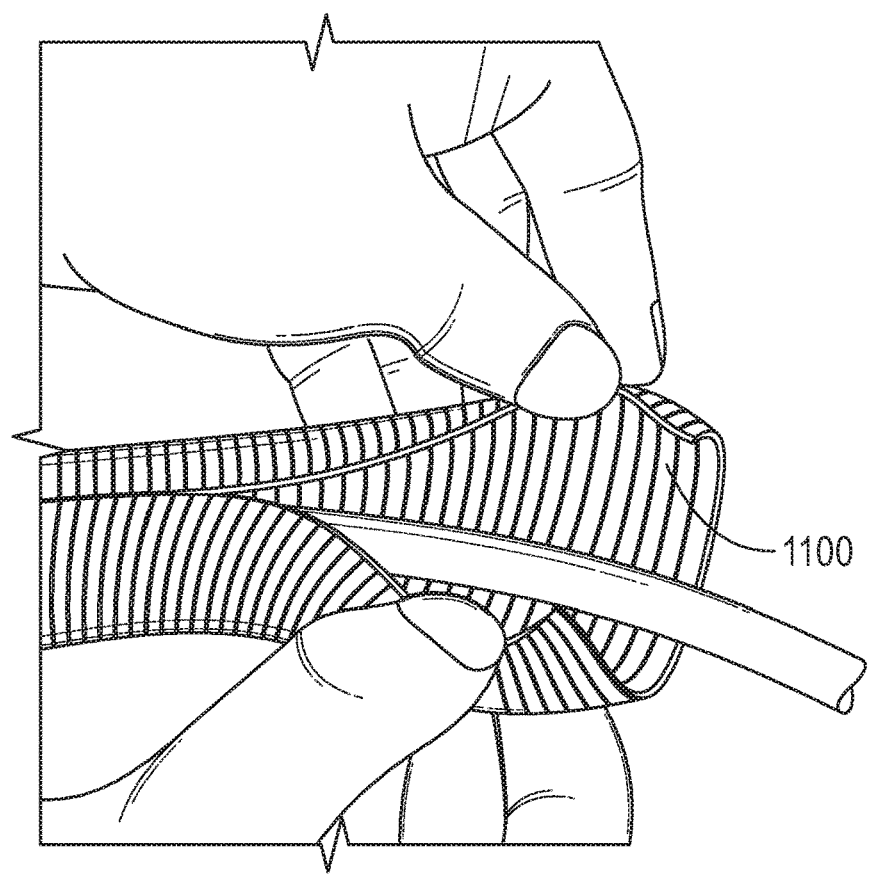

FIGS. 11A-11B are photographs of line protectors 1100 for a blood filtration system. The line protectors 1100 can be located around lines (e.g., the lines 104, 106, 114, 210 shown in FIG. 2, or the like) of a blood filtration system (e.g., the blood filtration system 100, shown in FIG. 1). The protectors 1100 can prevent compression of the lines of the blood filtration system and accordingly ensure flow of fluid (e.g., blood or filtrate fluid) through the lines.

Figure 12:
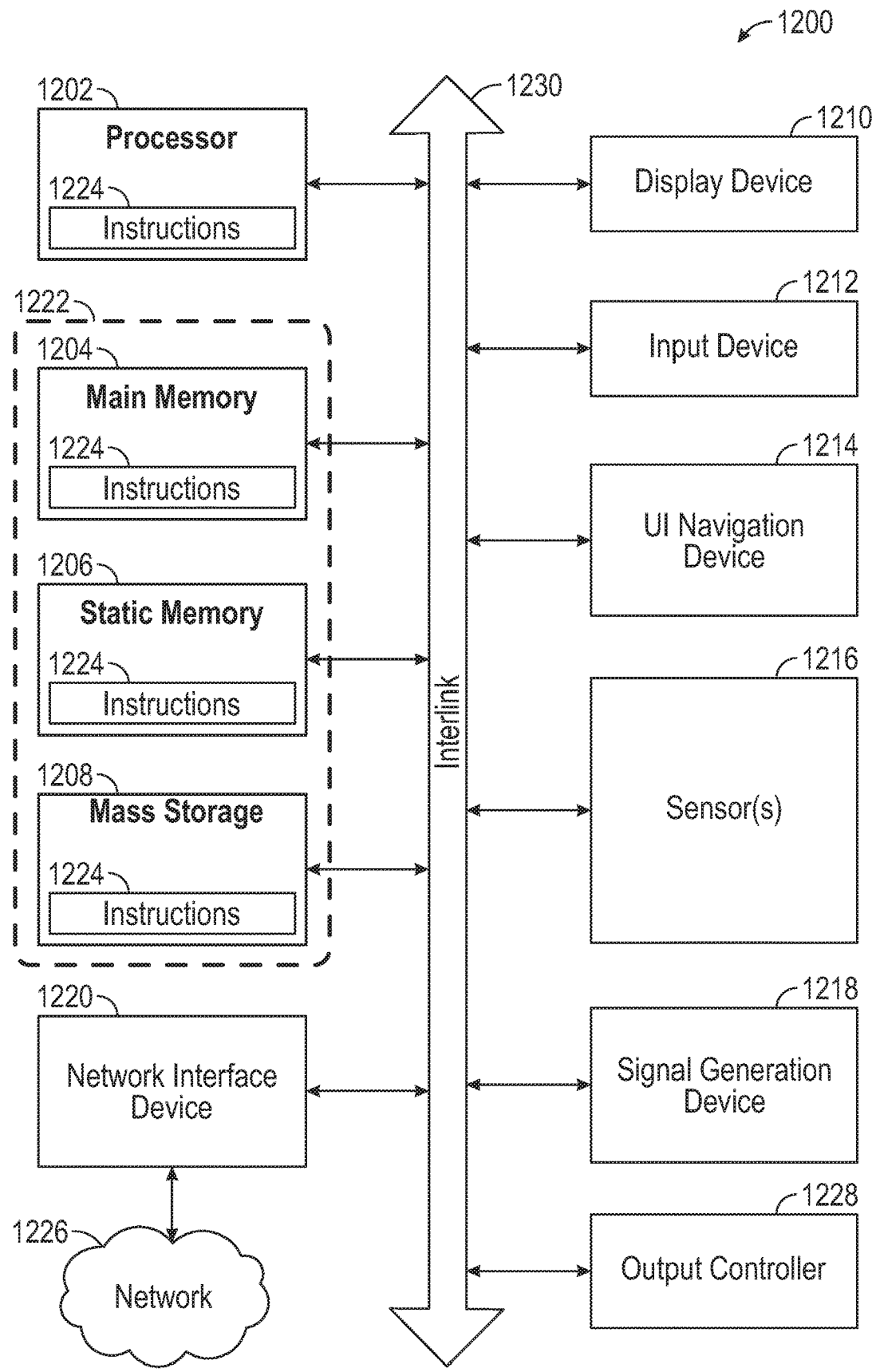
FIG. 12 is a block diagram illustrating an example of a machine upon which one or more embodiments can be implemented.

FIG. 12 illustrates a block diagram of an example machine 1200 upon which any one or more of the techniques (e.g., methodologies) discussed herein can perform, for instance the controller 102. Examples, as described herein, can include, or can operate by, logic or a number of components, or mechanisms in the machine 1200. Circuitry (e.g., processing circuitry) is a collection of circuits implemented in tangible entities of the machine 1200 that include hardware (e.g., simple circuits, gates, logic, etc.). Circuitry membership can be flexible over time. Circuitries include members that may, alone or in combination, perform specified operations when operating. In an example, hardware of the circuitry can be immutably designed to carry out a specific operation (e.g., hardwired). In an example, the hardware of the circuitry can include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components can be used in more than one member of more than one circuitry. For example, under operation, execution units can be used in a first circuit of a first circuitry at one point in time and reused by a second circuit in the first circuitry, or by a third circuit in a second circuitry at a different time. Additional examples of these components with respect to the machine 1200 follow.

In alternative embodiments, the machine 1200 can operate as a standalone device or can be connected (e.g., networked) to other machines. In a networked deployment, the machine 1200 can operate in the capacity of a server machine, a client machine, or both in server-client network environments. In an example, the machine 1200 can act as a peer machine in peer-to-peer (P2P) (or other distributed) network environment. The machine 1200 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1200 can include a hardware processor 1202 (e.g., a central processing unit (CPU), a graphics processing unit (GPU), a hardware processor core, or any combination thereof), a main memory 1204, a static memory (e.g., memory or storage for firmware, microcode, a basic-input-output (BIOS), unified extensible firmware interface (UEFI), etc.) 1206, and mass storage 1208 (e.g., hard drive, tape drive, flash storage, or other block devices) some or all of which can communicate with each other via an interlink (e.g., bus) 1230. The machine 1200 can further include a display unit 1210, an alphanumeric input device 1212 (e.g., a keyboard), and a user interface (UI) navigation device 1214 (e.g., a mouse). In an example, the display unit 1210, input device 1212 and UI navigation device 1214 can be a touch screen display. The machine 1200 can additionally include a storage device (e.g., drive unit) 1208, a signal generation device 1218 (e.g., a speaker), a network interface device 1220, and one or more sensors 1216, such as a global positioning system (GPS) sensor, compass, accelerometer, or other sensor. The machine 1200 can include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1202, the main memory 1204, the static memory 1206, or the mass storage 1208 can be, or include, a machine readable medium 1222 on which is stored one or more sets of data structures or instructions 1224 (e.g., software) embodying or utilized by any one or more of the techniques or functions described herein. The instructions 1224 can also reside, completely or at least partially, within any of registers of the processor 1202, the main memory 1204, the static memory 1206, or the mass storage 1208 during execution thereof by the machine 1200. In an example, one or any combination of the hardware processor 1202, the main memory 1204, the static memory 1206, or the mass storage 1208 can constitute the machine readable media 1222. While the machine readable medium 1222 is illustrated as a single medium, the term "machine readable medium" can include a single medium or multiple media (e.g., a centralized or distributed database, and/or associated caches and servers) configured to store the one or more instructions 1224.

The term "machine readable medium" can include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine readable medium examples can include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media can include: non-volatile memory, such as semiconductor memory devices (e.g., Electrically. Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 can be further transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1220 can include one or more physical jacks (e.g., Ethernet, coaxial, or phone jacks) or one or more antennas to connect to the communications network 1226. In an example, the network interface device 1220 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software. A transmission medium is a machine readable medium.

One or more of components, features, functions, or the like of the blood filtration systems (e.g., the blood filtration systems 100, 200, 400, 500, 700, 800, 900, 1000) described herein can be combined into one or more combinations, or sub-combinations. Additionally, one or more configurations of the controller 102 can be combined into or more combinations, or sub-combinations. Further, one or more configurations, techniques, or functions associated with the controller 102 can be included in a machine readable medium on which is stored one or more sets of data structures or instructions (e.g., software) embodying or utilized by any one or more of the techniques or functions described herein.

Figure 13:
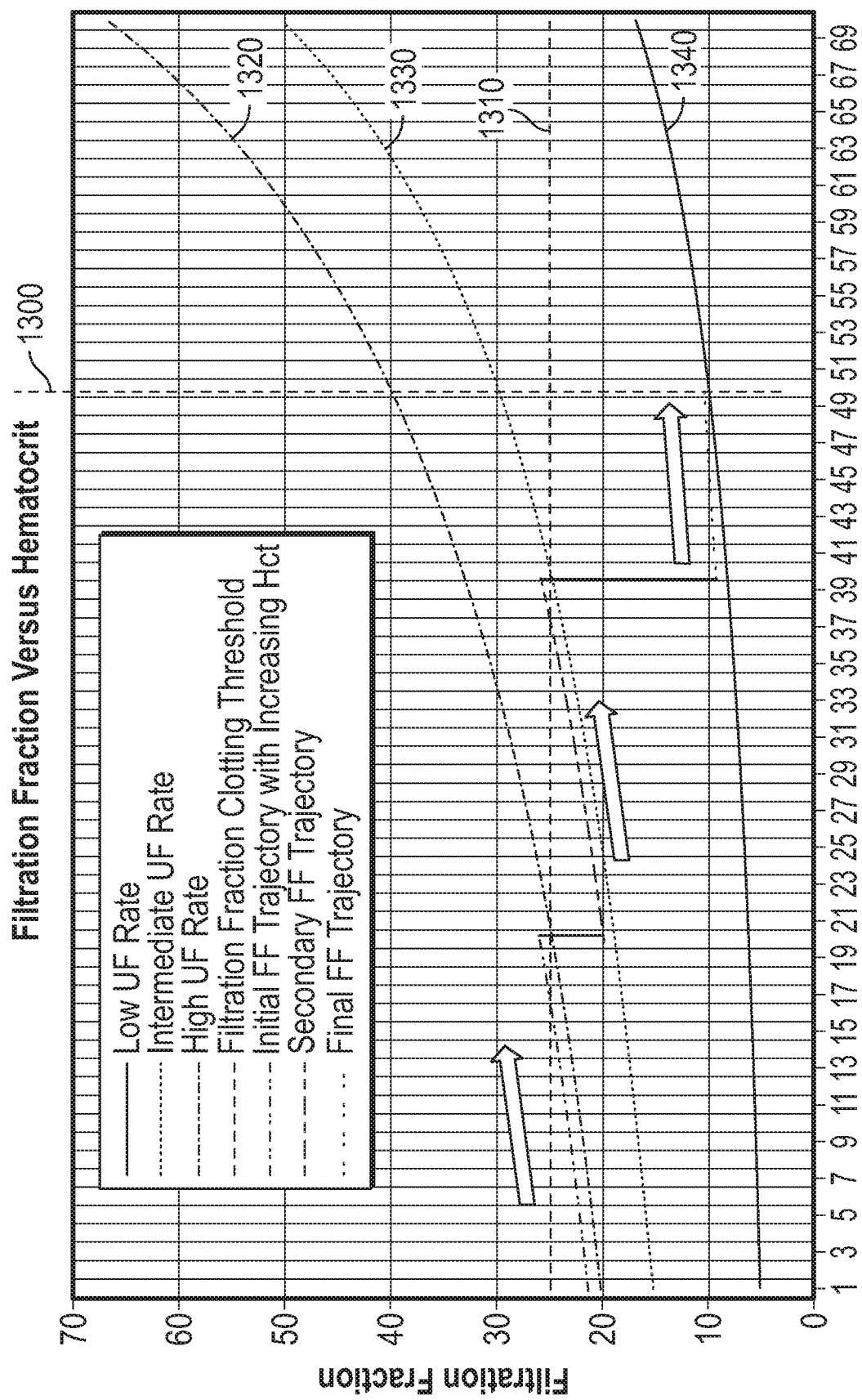
FIG. 13 shows a graph of a filtration fraction of a blood filtration system versus a hematocrit level of a patient.

FIG. 13 shows a graph of a filtration fraction of a blood filtration system versus a hematocrit level of a patient. As discussed herein, the hematocrit of the patient is determined according to Equation (1), and the filtration fraction of a blood filtration system is determined according to Equation (2). A blood filtration system (e.g., the blood filtration system 100 shown in FIG. 1) can include a hematocrit threshold 1300 (e.g., 50 percent, or within a range of 45 percent to 55 percent, or the like). Additionally, the blood filtration system can include a filtration fraction threshold 1310. In some examples, if the hematocrit threshold 1300, or the filtration fraction threshold 1310 are exceeded, a filter (e.g., the filter shown in FIG. 1) can become clogged, for instance due to blood clotting in the filter. Accordingly, the blood filtration system can be operated (e.g., by the controller 102) to maintain the filtration fraction below the filtration fraction threshold 1310, and can maintain a patient hematocrit value less than the hematocrit threshold 1300.

In an example, the filtration pump 116 (shown in FIG. 1) can be operated to vary a speed of the filtration pump (e.g., between 10-500 milliliters per hour). The speed of the filtration pump 116 can be varied incrementally (e.g., in 5 millimeter per hour increments). The controller 102 can operate the filtration pump 116 to vary the speed of the filtration pump 116, and accordingly maintain the filtration fraction below the filtration fraction threshold 1310. Additionally, the controller 102 can operate the blood pump 112 (shown in FIG. 1) to maintain the filtration fraction below the filtration fraction threshold 1310 (e.g., by varying the blood flow rate through the system). Further, the controller 102 can stop the filtration pump 116 (e.g., to stop therapy with the blood filtration system) if the hematocrit threshold 1300 is exceeded.

In an example, the blood filtration system can extract filtrate fluid at a high filtration rate (e.g., 400 milliliters per hour), as shown by a first curve 1320. As filtrate fluid is extracted from the patient, the hematocrit level of the patient increases, and the filtration fraction increases (because the denominator of Equation (1) is reduced). The blood filtration system can maintain the high filtration rate until the filtration fraction threshold 1310 is exceeded, and the blood filtration system can operate the filtration pump 116 at an intermediate filtration rate (e.g., 200 milliliters per hour), as shown by a second curve 1330. The blood filtration system can continue to extract filtrate fluid from blood of the patient at the intermediate filtration rate, and accordingly the hematocrit value of the patient can continue to increase. Accordingly, the filtration fraction continues to increase at the intermediate filtration rate. The blood filtration system can maintain the intermediate filtration rate until the filtration fraction threshold 1310 is exceeded.

Once the filtration fraction 1310 has been exceeded at the intermediate filtration rate, the blood filtration system can operate the filtration pump at a low filtration rate (e.g., 50 milliliters per hour), as shown by a third curve 1340. The blood filtration system can continue to extract filtrate fluid from blood of the patient at the low filtration rate, and accordingly the hematocrit value of the patient can continue to increase. The blood filtration system can maintain the low filtration rate until the hematocrit threshold 1300 is exceeded, and the blood filtration system can stop the filtration pump 116 (e.g., a filtration rate of 0 milliliters per second).

Once the hematocrit threshold 1300 has been exceeded, the blood pump 112 can continue to pump blood through the blood filtration system, and the blood filtration system can monitor the hematocrit value (or other health parameters of the patient) to determine if the patient requires additional therapy (e.g., extraction of filtrate fluid from the blood). For instance, the plasma refill rate of the patient can reduce the hematocrit value of the patient, and blood filtration system can resume therapy.

Figure 14:
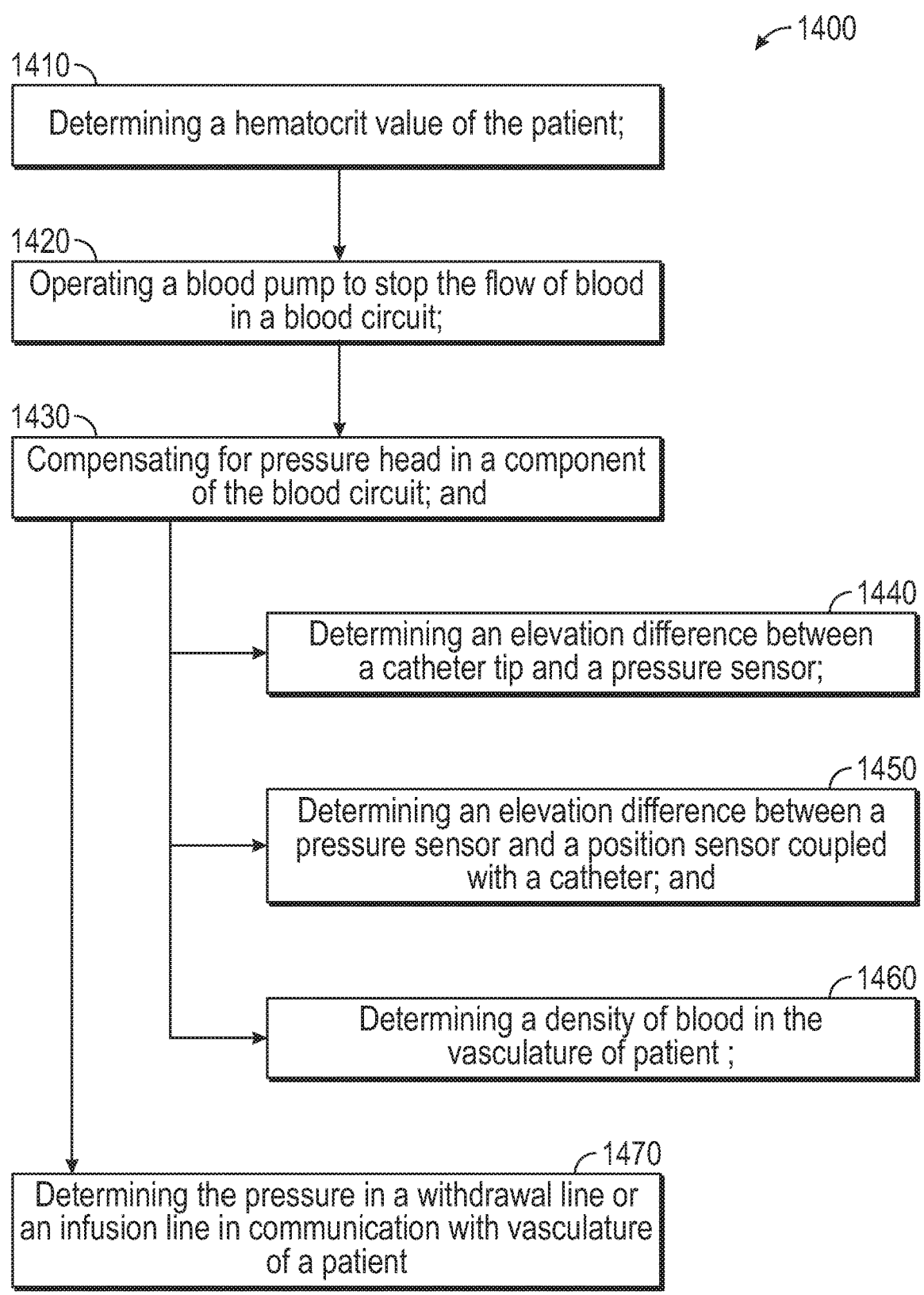
FIG. 14 shows a method for determining venous pressure of a patient with a blood filtration system.

FIG. 14 shows a method 1400 for determining venous pressure of a patient with a blood filtration system (e.g., the blood filtration system 100, or the like). In describing the method 300, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1400 include, but are not limited to, the corresponding numbered elements provided herein and other corresponding elements described herein (both numbered and unnumbered) as well as their equivalents. Additionally, the method 1400 can be included in instructions on a computer readable medium, and the instructions can be carried out by the controller 102 (e.g., processing circuitry).

At 1410, the method 1400 can include determining a hematocrit value of a patient, for example with the controller 102 (e.g., the controller 102 can communicate with the hematocrit sensor 126 to determine the hematocrit value). The method 1400 can include at 1420 that the blood pump 112 can be operated to stop a flow of blood in the blood circuit 140 (e.g., within the lines 104, 106).

At 1430, a pressure head in a component of the blood circuit 140 (e.g., one or more of the lines 104, 106, the catheter 108, or the like) can be compensated for when determining the venous pressure of the patient. For example, at 1440 an elevation difference between the catheter tip 130 and a pressure sensor (e.g., the sensor 124A) can be determined, for example with the system 100 (e.g., the controller 102 in communication with one or more position sensors). In another example, at 1450 an elevation difference between a pressure sensor (e.g., the sensor 124A) and a position sensor (e.g., the sensor 124D) can be determined (e.g., by determining the difference in elevation between the sensors 124A, 124D with the controller 102).

At 1460, a density of the blood of the patient can be determined. The determined head pressure in the blood circuit can correspond to (e.g., a variable in an equation that determines the head pressure, associated with, contribute to, based on, or the like) the density of the blood of the patient. Accordingly, determining the blood density can improve the accuracy of the head pressure compensation when determining the venous pressure of the patient.

At 1470, the method 1400 can include determining the pressure (e.g., with the sensors 124A, 124B) in a component of the blood circuit 140, for example the withdrawal line 104 or the infusion line 106. In an example, the catheter tip 130 is located within vasculature of the patient, and the system 100 can withdraw blood from (or infuse blood into) the vasculature of the patient. Accordingly, when the blood pump 112 is operated to stop the flow of blood in the blood circuit 140, the pressure in the lines 104, 106 can correspond to the pressure in the vasculature of the patient. As a result, the system 100 can determine the venous pressure in the vasculature of the patient with the sensors 124.

Various Notes

Aspect 1 is a blood filtration system for reducing one or more plasma constituents in blood of a patient, the system comprising: a variable-speed blood pump configured to pump blood in a withdrawal line, through a filter, and into an infusion line, wherein: the withdrawal line and the infusion line are configured to couple with a catheter, and the catheter is configured for insertion into a blood stream of the patient; the withdrawal line and the infusion line are configured to couple with the filter, and the filter is configured to reduce an amount of one or more plasma constituents in blood flowing through the filter and provide a filtrate fluid including the plasma constituents; a variable speed filtration pump configured to extract the filtrate fluid from the filter; and a controller including processing circuitry, wherein the controller is configured to: control the speed of the blood pump to vary a flow rate of the blood through the filter; control the speed of the filtration pump to vary the extraction rate of the filtrate fluid from the filter; determine a venous pressure of the patient; and provide a notification of the venous pressure of the patient.

In Aspect 2, the subject matter of Aspect 1 optionally includes wherein determining the venous pressure of the patient includes controlling the speed of the blood pump to stop the blood pump.

In Aspect 3, the subject matter of Aspect 2 optionally includes a first pressure sensor in communication with the withdrawal line and a second pressure sensor in communication with the infusion line, wherein determining the venous pressure of the patient includes determining a pressure differential between the first pressure sensor and the second pressure sensor, and providing the notification when the pressure differential exceeds a pressure differential threshold.

In Aspect 4, the subject matter of any one or more of Aspects 1-3 optionally include wherein the controller is configured to determine a hematocrit value of the patient, and the controller is further configured to set the extraction rate of filtrate fluid from the filter using the determined hematocrit value of the patient.

In Aspect 5, the subject matter of Aspect 4 optionally includes wherein determining the hematocrit value of the patient includes: controlling the speed of the blood pump and setting the flow rate of blood through the filter at a first blood flow rate; controlling the speed of the blood pump and setting the flow rate of blood through the filter at a second blood flow rate, wherein the first blood flow rate is different than the second blood flow rate; and determining the hematocrit at the second blood flow rate.

In Aspect 6, the subject matter of Aspect 5 optionally includes wherein determining the hematocrit value of the patient includes controlling the speed of the pump and setting the flow rate of blood through the filter at the first rate after determining the hematocrit value of the patient.

In Aspect 7, the subject matter of any one or more of Aspects 4-6 optionally include wherein the controller is configured to determine a red blood cell volume of the blood of the patient using the hematocrit value of the patient.

In Aspect 8, the subject matter of Aspect 7 optionally includes wherein determining the red blood cell volume of the blood of the patient includes: controlling a speed of the filtration pump by changing a filtration rate from a first filtration rate to a second filtration rate; determining a first rate of change of an inverse of the hematocrit value of the patient corresponding to the hematocrit value of the patient at the first filtration rate; determining a second rate of change of an inverse of the hematocrit value of the patient corresponding to the hematocrit value of the patient at the second filtration rate; and determining a difference between the first rate of change and the second rate of change.

In Aspect 9, the subject matter of any one or more of Aspects 7-8 optionally include wherein the controller is configured to: determine a filtrate fluid extraction volume corresponding to a volume of filtrate fluid extracted from the patient, wherein the filtrate fluid extraction volume is determined using the determined red blood cell volume; and determine a plasma refill rate of the patient according to the determined hematocrit value of the patient and the determined filtrate fluid extraction volume.

In Aspect 10, the subject matter of any one or more of Aspects 1-9 optionally include wherein determining the venous pressure of the patient includes compensating for a pressure head in the withdrawal line or the infusion line.

In Aspect 11, the subject matter of Aspect 10 optionally includes a first pressure sensor in communication with the withdrawal line and configured to measure the pressure in the withdrawal line, wherein the first pressure sensor is located remote from a catheter tip of the withdrawal line, and the controller is configured to determine the venous pressure of the patient at the catheter tip by compensating for the pressure head in the withdrawal line between the catheter tip and the first pressure sensor.

In Aspect 12, the subject matter of any one or more of Aspects 1-11 optionally include a blood circuit configured to couple with the blood filtration system, the blood circuit including the catheter, the withdrawal line, and infusion line; an activation key coupled with a portion of the blood circuit, wherein the activation key is in communication with the controller, and the controller provides an activated characteristic to the activation key when the blood circuit is coupled to the blood filtration system.

In Aspect 13, the subject matter of Aspect 12 optionally includes wherein the controller is configured to provide an expiration characteristic to the activation key after a specified time period from when the controller provided the activated characteristic to the activation key, and providing the activation key with the expiration characteristic inhibits operation of the blood filtration system.

Aspect 14 is a blood filtration system for reducing one or more plasma constituents in blood of a patient, the system comprising: a variable-speed blood pump configured to pump blood in a withdrawal line, through a filter, and into an infusion line, wherein: the withdrawal line and the infusion line are configured to couple with a catheter, and the catheter is configured for insertion into a blood stream of the patient; a controller including processing circuitry, wherein the controller is configured to: determine a withdrawal line resistance characteristic of the withdrawal line using a first pressure sensor in communication with the withdrawal line, the withdrawal line resistance characteristic corresponding to an amount of resistance to a flow of blood through the withdrawal line; determine an infusion line resistance characteristic of the infusion line using a second pressure sensor in communication with the infusion line, the infusion line resistance characteristic corresponding to an amount of resistance to a flow of blood through the infusion line; and provide a notification of one or more of the withdrawal line resistance characteristic or the infusion line resistance characteristic.

In Aspect 15, the subject matter of Aspect 14 optionally includes wherein the controller is configured to: determine a hematocrit value of the patient; determine a hemoconcentration resistance characteristic of the blood according to the determined hematocrit value of the patient, wherein the withdrawal line resistance characteristic or the infusion line resistance characteristic correspond in part to the hemoconcentration characteristic; and determine an occlusion resistance characteristic by subtracting the hemoconcentration resistance characteristic from the withdrawal line resistance characteristic or from the infusion line resistance characteristic. In Aspect 16, the subject matter of Aspect 15 optionally includes wherein the notification of the one or more of the withdrawal line resistance characteristic or the infusion line resistance characteristic includes the occlusion resistance characteristic.

In Aspect 17, the subject matter of any one or more of Aspects 15-16 optionally include wherein the controller is configured to provide a notification of the occlusion resistance characteristic.

In Aspect 18, the subject matter of any one or more of Aspects 15-17 optionally include wherein determining the hematocrit value of the patient includes: controlling the speed of the blood pump and setting a flow rate of blood through the filter at a first blood flow rate; controlling the speed of the blood pump and setting the flow rate of blood through the filter at a second blood flow rate, wherein the first blood flow rate is different than the second blood flow rate; and determining the hematocrit at the second blood flow rate.

In Aspect 19, the subject matter of any one or more of Aspects 14-18 optionally include wherein the controller is configured to: compare the infusion line resistance or the withdrawal line resistance to a resistance threshold; reduce a filtration rate or increase the blood flow rate if the withdrawal line resistance or the infusion line resistance exceeds the resistance threshold.

In Aspect 20, the subject matter of any one or more of Aspects 14-19 optionally include wherein the withdrawal line and the infusion line are configured to be in communication with the filter, and the filter is configured to reduce an amount of one or more plasma constituents in blood flowing through the filter and provide a filtrate fluid including the plasma constituents.

Aspect 21, the subject matter of Aspect 20 optionally includes wherein the controller is further configured to: control the speed of a filtration pump to vary the extraction rate of the filtrate fluid from the filter; vary the extraction rate from a first specified extraction rate; wait for a specified time period; monitor the withdrawal line resistance characteristic or the infusion line resistance characteristic; and provide a notification if the infusion line resistance characteristic or the withdrawal line resistance characteristic increases after the specified time period.

In Aspect 22, the subject matter of any one or more of Aspects 20-21 optionally include wherein the controller is configured to: vary a filtration rate for reducing the plasma constituents in the blood; wait for a specified time period; monitor the withdrawal line resistance or the infusion line resistance; and operate a harvesting pump to extract filtrate fluid from a filtrate reservoir and inject the filtrate fluid into an inlet of the filter to dilute the blood flowing through the filter.

In Aspect 23, the subject matter of any one or more of Aspects 14-22 optionally include wherein the controller is configured to: determine a venous pressure of the patient by determining a pressure differential between the first pressure sensor and the second pressure sensor; and provide a notification when the pressure differential exceeds a pressure differential threshold.

In Aspect 24, the subject matter of Aspect 23 optionally includes wherein determining the venous pressure of the patient includes compensating for a pressure head in the withdrawal line.

In Aspect 25, the subject matter of Aspect 24 optionally includes a first pressure sensor in communication with the withdrawal line and configured to measure the pressure in the withdrawal line, wherein the first pressure sensor is located remote from a catheter tip of the withdrawal line, and the controller is configured to determine the venous pressure of the patient at the catheter tip by compensating for the pressure head in the withdrawal line between the catheter tip and the first pressure sensor.

In Aspect 26, the subject matter of any one or more of Aspects 14-25 optionally include wherein the controller is further configured to determine a blood flow rate of the blood flowing through the filter.

Aspect 27 is a blood filtration system for reducing one or more plasma constituents in blood of a patient, the system comprising: a controller including processing circuitry, wherein the controller is configured to: determine a filter resistance of a filter, wherein the filter is configured to reduce an amount of one or more plasma constituents in blood flowing through the filter and provide a filtrate fluid including the plasma constituents; determine if the filter resistance of the filter exceeds a first filter resistance threshold; operate a harvesting pump to extract filtrate fluid from a filtrate reservoir and inject the filtrate fluid into an inlet of the filter to dilute the blood flowing through the filter; monitor the filter resistance of the filter; and operate the harvesting pump to stop injecting filtrate fluid into the inlet of the filter when the filter resistance exceeds a second filter resistance threshold.

In Aspect 28, the subject matter of Aspect 27 optionally includes wherein the controller is further configured to determine a blood flow rate of the blood flowing through the filter.

In Aspect 29, the subject matter of Aspect 28 optionally includes wherein the controller is further configured to: determine if the blood flow rate exceeds a first flow rate threshold; operate the harvesting pump to inject filtrate fluid into the inlet of the filter; monitor the blood flow rate; and operate the harvesting pump to stop injecting filtrate fluid into the inlet of the filter when the blood flow rate exceeds a second flow rate threshold.

In Aspect 30, the subject matter of any one or more of Aspects 27-29 optionally include wherein the controller is further configured to: monitor a rate of change of the filter resistance; compare the rate of change of the filter resistance to a rate of change threshold.

In Aspect 31, the subject matter of any one or more of Aspects 27-30 optionally include wherein the controller is configured to: determine a withdrawal line resistance characteristic of the withdrawal line using a first pressure sensor in communication with the withdrawal line, the withdrawal line resistance characteristic corresponding to an amount of resistance to a flow of blood through the withdrawal line; determine an infusion line resistance characteristic of the infusion line using a second pressure sensor in communication with the infusion line, the infusion line resistance characteristic corresponding to an amount of resistance to a flow of blood through the infusion line; and provide a notification of one or more of the withdrawal line resistance characteristic or the infusion line resistance characteristic.

In Aspect 32, the subject matter of Aspect 31 optionally includes wherein the controller is configured to: determine a hematocrit value of the patient; determine a hemoconcentration resistance characteristic of the blood according to the determined hematocrit value of the patient, wherein the withdrawal line resistance characteristic or the infusion line resistance characteristic correspond in part to the hemoconcentration characteristic; and determine an occlusion resistance characteristic by subtracting the hemoconcentration resistance characteristic from the withdrawal line resistance characteristic or from the infusion line resistance characteristic.

In Aspect 33, the subject matter of Aspect 32 optionally includes wherein the notification of the one or more of the withdrawal line resistance characteristic or the infusion line resistance characteristic includes the occlusion resistance characteristic.

In Aspect 34, the subject matter of any one or more of Aspects 32-33 optionally include wherein the controller is configured to provide a notification of the occlusion resistance characteristic.

In Aspect 35, the subject matter of any one or more of Aspects 32-34 optionally include wherein determining the hematocrit value of the patient includes: controlling a speed of the blood pump and setting a flow rate of blood through the filter at a first blood flow rate; controlling the speed of the blood pump and setting the flow rate of blood through the filter at a second blood flow rate, wherein the first blood flow rate is different than the second blood flow rate; and determining the hematocrit at the second blood flow rate.

In Aspect 36, the subject matter of any one or more of Aspects 31-35 optionally include wherein the controller is configured to: compare the infusion line resistance or the withdrawal line resistance to a resistance threshold; reduce a filtration rate or increase a blood flow rate if the withdrawal line resistance or the infusion line resistance exceeds the resistance threshold.

Aspect 37 is a blood filtration system for reducing one or more plasma constituents in blood of a patient, the system comprising: a first sensor configured to determine a hematocrit value of the patient; a second sensor configured to monitor movement of the patient relative to an initial position of the patient; a controller including processing circuitry, wherein the controller is configured to: monitor the hematocrit value of the patient; determine if the movement of the patient from the initial position affects the determined hematocrit value of the patient; and provide a notification if the hematocrit determination is affected by the movement of the patient.

In Aspect 38, the subject matter of Aspect 37 optionally includes wherein: the first sensor includes an accelerometer coupled with the patient, and the accelerometer is configured to monitor the movement of the patient by determining acceleration of a portion of a body of the patient; and determining if the movement of the patient from the initial position affects the determined hematocrit value of the patient includes comparing the acceleration of the portion of the body of the patient to an acceleration threshold.

In Aspect 39, the subject matter of any one or more of Aspects 37-38 optionally include wherein: the first sensor includes an accelerometer coupled with the patient, and the accelerometer is configured to monitor the movement of the patient by determining a change in position of a portion of a body of the patient; and determining if the movement of the patient from the initial position affects the determined hematocrit value of the patient includes comparing the change in position of the portion of the body of the patient to a positional threshold.

In Aspect 40, the subject matter of any one or more of Aspects 37-39 optionally include wherein: the first sensor includes an optical sensor coupled with the blood filtration system, and the optical sensor is configured to monitor the movement of the patient by observing a patient reference point; and determining if the movement of the patient from the initial position affects the determined hematocrit value of the patient includes: determining the position of the patient reference point relative to the optical sensor; determining a movement value, wherein the movement value is equal to a difference between the position of the patient reference point to the initial position; and comparing the movement value to a movement threshold.

In Aspect 41, the subject matter of any one or more of Aspects 37-40 optionally include wherein: the first sensor includes a pressure sensor in communication with a blood stream of the patient, and the first sensor is configured to monitor a change in pressure within the blood stream of the patient; determining if the movement of the patient from the initial position affects the determined hematocrit value of the patient includes comparing the change in pressure within the blood stream with a pressure threshold.

In Aspect 42, the subject matter of any one or more of Aspects 37-41 optionally include wherein the controller is further configured to apply a correction value to the determined hematocrit value according to the movement of the patient, wherein the correction value is determined by evaluating a change in the hematocrit value according to motion of the patient.

In Aspect 43, the subject matter of any one or more of Aspects 37-42 optionally include wherein the controller is configured to determine a venous pressure of the patient using the hematocrit value of the patient, and determining the venous pressure of the patient includes compensating for a pressure head in a withdrawal line or an infusion line.

In Aspect 44, the subject matter of Aspect 43 optionally includes a first pressure sensor in communication with the withdrawal line and configured to measure the pressure in the withdrawal line, wherein the first pressure sensor is located remote from a catheter tip of the withdrawal line, and the controller is configured to determine the venous pressure of the patient at the catheter tip by compensating for the pressure head in the withdrawal line between the catheter tip and the first pressure sensor.

Aspect 45 is a method for reducing one or more plasma constituents in blood of a patient, the method comprising: determining a red blood cell volume of the blood of the patient; inputting the red blood cell volume into a blood filtration system configured to a reduce an amount of one or more plasma constituents in the blood of the patient; and determining a hematocrit value of the patient, wherein the red blood cell volume is associated with the hematocrit value of the patient.

In Aspect 46, the subject matter of Aspect 45 optionally includes wherein determining the red blood cell volume of the blood of the patient includes: injecting a tracer into a blood stream of the patient; and withdrawing one or more blood samples from the blood stream of the patient.

In Aspect 47, the subject matter of any one or more of Aspects 45-46 optionally include wherein determining the red blood cell volume of the blood of the patient includes: controlling a speed of a filtration pump configured to extract a filtrate fluid including one or more plasma constituents from a filter by changing a filtration rate from a first filtration rate to a second filtration rate; determining a first rate of change of an inverse of the hematocrit value of the patient corresponding to the hematocrit value of the patient at the first filtration rate; determining a second rate of change of an inverse of the hematocrit value of the patient corresponding to the hematocrit value of the patient at the second filtration rate; and determining a difference between the first rate of change and the second rate of change.

Aspect 48 is a blood filtration system for reducing one or more plasma constituents in blood of a patient, the system comprising: a controller including processing circuitry, wherein the controller is configured to: monitor a hematocrit value of the patient; control a speed of one or more pumps to adjust a filtration fraction, wherein: the filtration fraction includes a ratio of a filtration rate to a blood flow rate through a filter; the filtration rate includes a rate that one or more plasma constituents is extracted from the filter; and the blood flow rate includes a rate that blood flows through the filter; compare the hematocrit value to a hematocrit threshold; and maintain the filtration fraction when the hematocrit value equals the hematocrit threshold.

In Aspect 49, the subject matter of Aspect 48 optionally includes wherein the controller is further configured to control a speed of a filtration pump to adjust the filtration fraction.

In Aspect 50, the subject matter of any one or more of Aspects 48-49 optionally include wherein the controller is further configured to control a speed of a blood pump to adjust the filtration fraction.

Aspect 51 is a blood filtration system for reducing one or more plasma constituents in blood of a patient, the system comprising: a controller including processing circuitry, wherein the controller is configured to: monitor a longitudinal filter resistance of a filter configured to reduce an amount of one or more plasma constituents in blood flowing through the filter and provide a filtrate fluid including the plasma constituents, monitoring the longitudinal filter resistance including: determining a first pressure differential between a blood inlet pressure at an inlet port of the filter and a filtration fluid pressure at a filtration fluid port of the filter; determining a ratio of the first pressure differential to a blood flow rate of the blood flowing through the filter.

In Aspect 52, the subject matter of Aspect 51 optionally includes wherein the controller is further configured to: monitor a transverse resistance of the filter, monitoring the transverse resistance including: determine a second pressure differential between a blood outlet pressure at a blood outlet port of the filter and the filtration fluid pressure; determine a ratio of the second pressure differential to a filtrate flow rate, wherein the filtrate flow rate corresponds to a rate that filtrate fluid is removed from the filter.

Aspect 53 is a blood filtration system for reducing one or more plasma constituents in blood of a patient, the system comprising: a filter configured to reduce an amount of one or more plasma constituents in blood flowing through the filter and provide a filtrate fluid including the plasma constituents, wherein the filter includes: a filter body; a blood inlet port included in the filter body and configured to couple with a withdrawal line, wherein the withdrawal line is configured to couple with a catheter and transmit blood from the patient; a blood outlet port included in the filter body and configured to couple with an infusion line, wherein the infusion line is configured to couple with the catheter and transmit blood to the patient; and a filtrate fluid port included in the filter body and configured to couple with a harvest fluid line, wherein the filter is configured to transmit extracted filtrate fluid to the filtrate fluid port.

In Aspect 54, the subject matter of Aspect 53 optionally includes wherein the harvesting port is included in the filter body.

In Aspect 55, the subject matter of any one or more of Aspects 53-54 optionally include wherein the harvesting port is coupled with the blood inlet port.

In Aspect 56, the subject matter of any one or more of Aspects 53-55 optionally include the catheter configured for insertion into a blood stream of the patient.

Aspect 57 is a blood filtration system for reducing one or more plasma constituents in blood of a patient, the system comprising: a withdrawal line configured to couple with a catheter and transmit blood from the patient, the withdrawal line in communication with a first valve configured to stop blood flow in the withdrawal line; an infusion line configured to couple with the catheter and transmit blood to the patient, the infusion line in communication with a second valve configured to stop blood flow in the infusion line; a filtration line configured to transmit a filtrate fluid including the one or more plasma constituents, the filtration line in communication with a third valve configured to stop flow of the filtrate fluid in the filtration line; a filter configured to reduce an amount of the one or more plasma constituents in blood flowing through the filter and provide filtrate fluid including the plasma constituents, the filter including: a filter body; a blood inlet port included in the filter body and configured to couple with a withdrawal line, the blood inlet port in communication with a fourth valve configured to stop flow of blood from the blood inlet port; a blood outlet port included in the filter body and configured to couple with the infusion line, the blood outlet port in communication with a fifth valve configured to stop flow of blood from the blood outlet port; and a filtrate fluid port included in the filter body and configured to couple with the filtration line, wherein the filter is configured to transmit the filtrate fluid to the filtrate fluid port, and the filtrate fluid port is in communication with a sixth valve configured to stop flow of filtrate fluid from the filtrate fluid port.

In Aspect 58, the subject matter of Aspect 57 optionally includes a harvesting port configured to receive filtrate fluid from the filtrate fluid port, the harvesting port in communication with the blood inlet port and a seventh valve, the seventh valve configured to stop flow of filtrate fluid or blood from the harvesting port.

Aspect 59 is a blood filtration system for reducing one or more plasma constituents in blood of a patient, the system comprising: a blood pump in communication with a blood reservoir; a filtration pump configured to couple with a filter, wherein the filter is configured to reduce an amount of one or more plasma constituents in blood flowing through the filter and provide a filtrate fluid including the plasma constituents; and a controller including processing circuitry, wherein the controller is configured to: control the blood pump to operate the blood pump in a first flow direction to transmit blood from the patient into the blood reservoir; control the blood pump to transmit blood from the blood reservoir to the filter, controlling the blood pump to transmit blood from the blood reservoir includes operating the blood pump in a second flow direction; and control the filtration pump to extract filtration fluid from the filter and transmit the extracted filtration fluid to a filtrate fluid reservoir.

In Aspect 60, the subject matter of Aspect 59 optionally includes a withdrawal line configured to couple with a catheter, the withdrawal line including at least one check valve, the at least one check valve configured to provide unidirectional flow of blood within the withdrawal line.

In Aspect 61, the subject matter of Aspect 60 optionally includes wherein the at least one check valve is configured to prevent blood from flowing to the catheter when the blood pump transmits blood from the blood reservoir to the filter.

In Aspect 62, the subject matter of any one or more of Aspects 59-61 optionally include wherein the blood pump is a peristaltic pump.

Aspect 63 is a blood filtration system for reducing one or more plasma constituents in blood of a patient, the system comprising: a controller including processing circuitry, wherein the controller is configured to: control a speed of a blood pump in communication with the controller, to vary a flow rate of blood through a filter to reduce an amount of one or more plasma constituents in blood flowing through the filter and provide a filtrate fluid including the plasma constituents; control the speed of a harvest pump to vary an extraction rate of filtrate fluid from a filtrate reservoir; determine a venous pressure of the patient; and provide a notification of the venous pressure of the patient.

Aspect 64 can include or use, or can optionally be combined with any portion or combination of any portions of any one or more of Aspects 1 through 63 to include or use, subject matter that can include means for performing any one or more of the functions of Aspects 1 through 63, or a machine-readable medium including instructions that, when performed by a machine, cause the machine to perform any one or more of the functions of Aspects 1 through 63.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A blood filtration system for reducing one or more plasma constituents in blood of a patient, the system comprising:
a variable-speed blood pump configured to pump blood in a withdrawal line, through a filter, and into an infusion line, wherein:
the withdrawal line and the infusion line are configured to couple with a catheter, and the catheter is configured for insertion into a blood stream of the patient and
the withdrawal line and the infusion line are configured to couple with the filter, and the filter is configured to reduce an amount of one or more plasma constituents in blood flowing through the filter and provide a filtrate fluid including the plasma constituents;
a first pressure sensor in communication with the withdrawal line;
a second pressure sensor in communication with the infusion line;
a variable speed filtration pump configured to extract the filtrate fluid from the filter at an extraction rate, and the extraction rate is variable according to a speed of the filtration pump; and
a controller including processing circuitry, wherein the controller is configured to:
adjust a speed of the blood pump to vary a flow rate of the blood through the filter;
adjust a speed of the filtration pump to vary the extraction rate of the filtrate fluid from the filter;
determine a venous pressure of the patient, wherein determining the venous pressure of the patient includes determining a pressure differential between the first pressure sensor and the second pressure sensor; and
provide a notification of the venous pressure of the patient.

2. The blood filtration system of claim 1, wherein the controller determining the venous pressure of the patient includes the controller adjusting the speed of the blood pump to stop the blood pump and the controller determines the venous pressure of the patient while the blood pump is stopped.

3. The blood filtration system of claim 1, wherein the controller is configured to provide the notification when the pressure differential exceeds a pressure differential threshold.

4. The blood filtration system of claim 1, wherein the controller is configured to determine a hematocrit value of the patient, and the controller is further configured to operate the filtration pump to vary the extraction rate based on the hematocrit value of the patient.

5. The blood filtration system of claim 4, wherein the controller determining the hematocrit value of the patient includes the controller:
adjusting the speed of the blood pump and setting the flow rate of blood through the filter at a first blood flow rate;
adjusting the speed of the blood pump and setting the flow rate of blood through the filter at a second blood flow rate, wherein the first blood flow rate is different than the second blood flow rate; and
determining the hematocrit at the second blood flow rate.

6. The blood filtration system of claim 5, wherein the controller determining the hematocrit value of the patient includes the controller adjusting the speed of the blood pump and setting the flow rate of blood through the filter at the first blood flow rate after determining the hematocrit value of the patient.

7. The blood filtration system of claim 4, wherein the controller is configured to determine a red blood cell volume of the blood of the patient using the hematocrit value of the patient.

8. The blood filtration system of claim 7, wherein the controller determining the red blood cell volume of the blood of the patient includes the controller:
adjusting a speed of the filtration pump by changing a filtration rate from a first filtration rate to a second filtration rate;
determining a first rate of change of an inverse of the hematocrit value of the patient corresponding to the hematocrit value of the patient at the first filtration rate;
determining a second rate of change of an inverse of the hematocrit value of the patient corresponding to the hematocrit value of the patient at the second filtration rate; and
determining a difference between the first rate of change and the second rate of change.

9. The blood filtration system of claim 7, wherein the controller is configured to:
   determine a filtrate fluid extraction volume corresponding to a volume of filtrate fluid extracted from the patient, wherein the filtrate fluid extraction volume is determined using the determined red blood cell volume; and
   determine a plasma refill rate of the patient according to the determined hematocrit value of the patient and the determined filtrate fluid extraction volume.

10. The blood filtration system of claim 1, wherein the controller determining the venous pressure of the patient includes the controller compensating for a pressure head in the withdrawal line or the infusion line.

11. The blood filtration system of claim 10, wherein the first pressure sensor is located remote from a catheter tip of the withdrawal line, and the controller is configured to determine the venous pressure of the patient at the catheter tip by compensating for the pressure head in the withdrawal line between the catheter tip and the first pressure sensor.

12. The blood filtration system of claim 1, further comprising:
   a blood circuit configured to couple with the blood filtration system, the blood circuit including the catheter, the withdrawal line, and infusion line;
   an activation key coupled with a portion of the blood circuit, wherein the activation key is in communication with the controller, and the controller provides an activated characteristic to the activation key when the blood circuit is coupled to the blood filtration system.

13. The blood filtration system of claim 12, wherein the controller is configured to provide an expiration characteristic to the activation key after a specified time period from when the controller provided the activated characteristic to the activation key, and providing the activation key with the expiration characteristic inhibits operation of the blood filtration system.

14. A system comprising:
   a first pressure sensor configured to determine pressure in a withdrawal line, the withdrawal line configured to receive blood from vasculature of a patient;
   a second pressure sensor configured to determine pressure in an infusion line, the infusion line configured to infuse blood into the vasculature of the patient; and
   a controller in communication with the first pressure sensor and the second pressure sensor, wherein the controller is configured to:
      determine a pressure differential between the first pressure sensor and the second pressure sensor; and
      determine a venous pressure of the patient using the pressure differential between the first pressure sensor and the second pressure sensor.

15. The system of claim 14, wherein the controller determining the venous pressure of the patient includes the controller compensating for a pressure head in the withdrawal line or the infusion line.

16. The system of claim 15, wherein the first pressure sensor is located remote from an end of the withdrawal line, and the controller is configured to determine the venous pressure of the patient by compensating for the pressure head in the withdrawal line between the end of the withdrawal line and the first pressure sensor.

17. The system of claim 15, wherein the controller compensating for a pressure head in the withdrawal line or the infusion line includes the controller determining density of the blood in the withdrawal line, the infusion line, or both of the withdrawal line and the infusion line.

18. The system of claim 14, wherein the controller is configured to:
   compare the pressure differential between the first pressure sensor and the second pressure sensor to a pressure differential threshold; and
   provide a notification if the pressure differential between the first pressure sensor and the second pressure sensor exceeds the pressure differential threshold.

19. The system of claim of claim 14, wherein the system comprises a blood filtration system, and the blood filtration system includes a filter configured for communication with the withdrawal line, the infusion line, or both of the withdrawal line and the infusion line.

* * * * *